United States Patent
Kennedy, II et al.

(10) Patent No.: US 8,226,730 B2
(45) Date of Patent: Jul. 24, 2012

(54) SURGICAL IMPLANT

(75) Inventors: Kenneth C. Kennedy, II, Rathkeale (IE); LiKang Chin, Cleveland Heights, OH (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/817,956

(22) Filed: Jun. 17, 2010

(65) Prior Publication Data

US 2010/0256778 A1    Oct. 7, 2010

Related U.S. Application Data

(63) Continuation of application No. 10/915,626, filed on Aug. 10, 2004, now abandoned.

(60) Provisional application No. 60/494,613, filed on Aug. 11, 2003, provisional application No. 60/558,163, filed on Mar. 31, 2004.

(51) Int. Cl.
*A61F 2/02* (2006.01)

(52) U.S. Cl. .............. 623/23.72; 604/264; 606/191; 600/29

(58) Field of Classification Search .... 623/23.64–23.72; 606/157, 191, 108, 114–116, 153, 185; 600/114–116, 7, 9, 19, 16, 17, 29–32; 604/11, 604/264

See application file for complete search history.

(56) References Cited

U.S. PATENT DOCUMENTS

| | | | | |
|---|---|---|---|---|
| 1,867,624 A | * | 7/1932 | Hoffman | 600/567 |
| 1,969,671 A | * | 8/1934 | Nelson | 604/14 |
| 2,831,485 A | * | 4/1958 | Haeseler | 604/385.18 |
| 3,094,122 A | * | 6/1963 | Gauthier et al. | 604/164.01 |
| 3,818,894 A | | 6/1974 | Wichterle et al. | |
| 3,965,905 A | * | 6/1976 | Schoenholz et al. | 604/15 |
| 4,209,009 A | * | 6/1980 | Hennig | 600/30 |
| 4,479,791 A | * | 10/1984 | Sprague | 604/14 |
| 4,675,683 A | | 6/1987 | Robinson et al. | |
| 4,773,393 A | * | 9/1988 | Haber et al. | 600/30 |
| 4,786,276 A | * | 11/1988 | Haber | 600/31 |
| 4,800,900 A | * | 1/1989 | French | 128/885 |
| 4,815,449 A | * | 3/1989 | Horowitz | 600/7 |
| 4,832,680 A | * | 5/1989 | Haber et al. | 600/31 |
| 4,973,302 A | * | 11/1990 | Armour et al. | 604/15 |
| 4,978,323 A | * | 12/1990 | Freedman | 600/12 |

(Continued)

FOREIGN PATENT DOCUMENTS

CA    1 019 638 A1    10/1977

(Continued)

OTHER PUBLICATIONS

European Search Report completed Jun. 26, 2009 for European Application No. 09 15 9223.

(Continued)

*Primary Examiner* — Alvin J. Stewart

(74) *Attorney, Agent, or Firm* — Brinks Hofer Gilson & Lione

(57) ABSTRACT

An implant is disclosed including a bio-compatible implant body that can be provided with a tip, or interconnected by one or more filaments. The implant body can be formed of a variety of biocompatible materials, including bio-remodelable materials such as small intestine submucosa. Methods are disclosed for assembly of the implant. Additionally, a method is disclosed for delivering the implant to a desired location in a patient.

16 Claims, 22 Drawing Sheets

U.S. PATENT DOCUMENTS

| | | | | |
|---|---|---|---|---|
| 5,013,292 A | * | 5/1991 | Lemay | 600/30 |
| 5,041,077 A | * | 8/1991 | Kulick | 600/29 |
| 5,082,006 A | * | 1/1992 | Jonasson | 128/885 |
| 5,193,263 A | * | 3/1993 | Takahashi | 29/447 |
| 5,207,695 A | | 5/1993 | Trout, III | |
| 5,224,497 A | * | 7/1993 | Ehlers | 128/898 |
| 5,304,123 A | | 4/1994 | Atala et al. | |
| 5,336,263 A | | 8/1994 | Ersek et al. | |
| 5,350,354 A | * | 9/1994 | Billmers | 604/11 |
| 5,518,498 A | * | 5/1996 | Lindenberg et al. | 600/30 |
| 5,584,827 A | * | 12/1996 | Korteweg et al. | 604/369 |
| 5,601,557 A | * | 2/1997 | Hayhurst | 606/232 |
| 5,618,256 A | * | 4/1997 | Reimer | 600/29 |
| 5,681,334 A | * | 10/1997 | Evans et al. | 606/148 |
| 5,722,931 A | * | 3/1998 | Heaven | 600/29 |
| 5,749,826 A | * | 5/1998 | Faulkner | 600/29 |
| 5,755,706 A | * | 5/1998 | Kronenthal et al. | 604/358 |
| 5,785,680 A | | 7/1998 | Niezink et al. | |
| 5,820,628 A | * | 10/1998 | Middleman et al. | 606/147 |
| 5,906,575 A | * | 5/1999 | Conway et al. | 600/29 |
| 5,964,806 A | * | 10/1999 | Cook et al. | 623/11.11 |
| 6,056,687 A | * | 5/2000 | Polyak et al. | 600/29 |
| 6,067,991 A | * | 5/2000 | Forsell | 128/899 |
| 6,098,629 A | * | 8/2000 | Johnson et al. | 128/897 |
| 6,102,848 A | * | 8/2000 | Porter | 600/29 |
| 6,119,697 A | * | 9/2000 | Engel et al. | 128/885 |
| 6,167,886 B1 | * | 1/2001 | Engel et al. | 128/885 |
| 6,238,403 B1 | * | 5/2001 | Greene et al. | 606/108 |
| 6,251,063 B1 | * | 6/2001 | Silverman et al. | 600/29 |
| 6,251,064 B1 | * | 6/2001 | Silverman et al. | 600/29 |
| 6,264,600 B1 | * | 7/2001 | Grimm | 600/7 |
| 6,299,619 B1 | | 10/2001 | Greene, Jr. et al. | |
| 6,306,094 B1 | * | 10/2001 | Joseph | 600/458 |
| 6,338,345 B1 | * | 1/2002 | Johnson et al. | 128/897 |
| 6,354,989 B1 | * | 3/2002 | Nudeshima | 600/3 |
| 6,358,284 B1 | | 3/2002 | Fearnot et al. | |
| 6,401,718 B1 | * | 6/2002 | Johnson et al. | 128/897 |
| 6,402,677 B1 | * | 6/2002 | Jacobs | 600/7 |
| 6,419,701 B1 | * | 7/2002 | Cook et al. | 623/14.13 |
| 6,432,040 B1 | * | 8/2002 | Meah | 600/37 |
| 6,450,937 B1 | * | 9/2002 | Mercereau et al. | 600/7 |
| 6,450,938 B1 | * | 9/2002 | Miller | 600/7 |
| 6,497,646 B1 | * | 12/2002 | Candelaria et al. | 600/7 |
| 6,530,879 B1 | * | 3/2003 | Adamkiewicz | 600/30 |
| 6,554,760 B2 | * | 4/2003 | Lamoureux et al. | 600/7 |
| 6,558,309 B2 | * | 5/2003 | Hogendijk et al. | 600/7 |
| 6,572,525 B1 | * | 6/2003 | Yoshizumi | 600/7 |
| 6,592,859 B1 | * | 7/2003 | Bley | 424/78.08 |
| 6,595,909 B2 | * | 7/2003 | Silverman et al. | 600/29 |
| 6,595,911 B2 | * | 7/2003 | LoVuolo | 600/30 |
| 6,599,310 B2 | * | 7/2003 | Leung et al. | 606/228 |
| 6,599,311 B1 | * | 7/2003 | Biggs et al. | 606/232 |
| 6,604,529 B2 | * | 8/2003 | Kim | 128/899 |
| 6,689,047 B2 | * | 2/2004 | Gellman | 600/30 |
| 6,695,764 B2 | * | 2/2004 | Silverman et al. | 600/29 |
| 6,725,866 B2 | * | 4/2004 | Johnson et al. | 128/897 |
| 6,730,014 B2 | * | 5/2004 | Wilk | 600/12 |
| 6,830,576 B2 | * | 12/2004 | Fleischman et al. | 606/139 |
| 6,902,570 B2 | * | 6/2005 | Schraft et al. | 606/144 |
| 6,979,337 B2 | * | 12/2005 | Kato | 606/149 |
| 7,047,979 B2 | * | 5/2006 | Conrad et al. | 128/897 |
| 7,047,981 B2 | * | 5/2006 | Durgin | 128/898 |
| 7,056,277 B2 | * | 6/2006 | Silverman et al. | 600/29 |
| 7,104,945 B2 | * | 9/2006 | Miller | 600/7 |
| 7,150,709 B1 | * | 12/2006 | Schmidt et al. | 600/7 |
| 7,166,122 B2 | * | 1/2007 | Aganon et al. | 606/200 |
| 7,175,589 B2 | * | 2/2007 | Deem et al. | 600/30 |
| 7,175,638 B2 | * | 2/2007 | Gannoe et al. | 606/153 |
| 7,235,078 B2 | | 6/2007 | West, Jr. | |
| 7,237,553 B2 | * | 7/2007 | Knudson et al. | 128/897 |
| 7,241,274 B2 | * | 7/2007 | Suga | 604/15 |
| 7,244,270 B2 | * | 7/2007 | Lesh | 623/1.11 |
| 7,288,099 B2 | * | 10/2007 | Deem et al. | 606/151 |
| 7,288,101 B2 | * | 10/2007 | Deem et al. | 606/153 |
| 7,305,993 B2 | * | 12/2007 | Tropsha et al. | 128/897 |
| 7,328,707 B2 | * | 2/2008 | Durgin | 128/887 |
| 7,361,135 B2 | * | 4/2008 | Drobnik et al. | 600/3 |
| 7,371,215 B2 | * | 5/2008 | Colliou et al. | 600/300 |
| D572,362 S | * | 7/2008 | Edgett et al. | D24/141 |
| 7,449,020 B2 | * | 11/2008 | Edwards et al. | 606/28 |
| 7,488,335 B2 | * | 2/2009 | Sgro | 606/144 |
| 7,632,313 B2 | * | 12/2009 | Bhatnagar et al. | 623/17.16 |
| 7,641,688 B2 | * | 1/2010 | Lesh | 623/11.11 |
| 7,651,509 B2 | * | 1/2010 | Bojarski et al. | 606/139 |
| 7,666,205 B2 | * | 2/2010 | Weikel et al. | 606/192 |
| 7,695,427 B2 | * | 4/2010 | Kugler et al. | 600/37 |
| 7,708,752 B2 | * | 5/2010 | Durgin | 606/191 |
| 7,736,392 B2 | * | 6/2010 | Starkebaum | 623/23.64 |
| 7,749,151 B2 | * | 7/2010 | Ferguson | 600/7 |
| 7,756,582 B2 | * | 7/2010 | Imran et al. | 607/40 |
| 7,763,459 B2 | * | 7/2010 | Padmini et al. | 435/325 |
| 7,771,347 B2 | * | 8/2010 | Silverman et al. | 600/29 |
| 7,795,027 B2 | * | 9/2010 | Hiles | 435/395 |
| D626,650 S | * | 11/2010 | Edgett et al. | D24/141 |
| 7,824,701 B2 | * | 11/2010 | Binette et al. | 424/423 |
| 7,833,281 B2 | * | 11/2010 | Lehman et al. | 623/23.7 |
| 7,846,180 B2 | * | 12/2010 | Cerier | 606/232 |
| 7,862,502 B2 | * | 1/2011 | Pool et al. | 600/37 |
| 7,875,041 B2 | * | 1/2011 | Mikkaichi et al. | 606/144 |
| 7,875,296 B2 | * | 1/2011 | Binette et al. | 424/549 |
| 7,942,887 B2 | * | 5/2011 | Kraemer et al. | 606/151 |
| 7,947,055 B2 | * | 5/2011 | Gannoe et al. | 606/153 |
| 7,984,717 B2 | * | 7/2011 | Tropsha et al. | 128/897 |
| 8,007,427 B2 | * | 8/2011 | Reed et al. | 600/7 |
| D647,612 S | * | 10/2011 | Smet | D24/125 |
| 8,048,053 B2 | * | 11/2011 | Minoguchi et al. | 604/385.17 |
| 8,057,384 B2 | * | 11/2011 | Demarais | 600/37 |
| 8,066,689 B2 | * | 11/2011 | Mitelberg et al. | 604/509 |
| 8,070,670 B2 | * | 12/2011 | Deem et al. | 600/30 |
| 8,075,532 B2 | * | 12/2011 | Kassab et al. | 604/176 |
| 8,080,025 B2 | * | 12/2011 | Deem et al. | 606/153 |
| 8,123,768 B2 | * | 2/2012 | Vardi | 606/153 |
| 2002/0028979 A1 | * | 3/2002 | Silverman et al. | 600/29 |
| 2002/0072720 A1 | | 6/2002 | Hague et al. | |
| 2002/0091295 A1 | * | 7/2002 | Wilk | 600/12 |
| 2002/0183768 A1 | * | 12/2002 | Deem et al. | 606/151 |
| 2003/0013934 A1 | * | 1/2003 | Schmidt | 600/7 |
| 2003/0015203 A1 | * | 1/2003 | Makower et al. | 128/831 |
| 2003/0018233 A1 | * | 1/2003 | Miller | 600/7 |
| 2003/0073948 A1 | * | 4/2003 | Binner et al. | 604/15 |
| 2003/0153806 A1 | * | 8/2003 | Miller | 600/30 |
| 2003/0158601 A1 | * | 8/2003 | Silverman et al. | 623/14.13 |
| 2003/0188755 A1 | * | 10/2003 | Milbocker | 128/898 |
| 2003/0192558 A1 | * | 10/2003 | Durgin | 128/898 |
| 2003/0212419 A1 | * | 11/2003 | West | 606/157 |
| 2004/0019388 A1 | * | 1/2004 | Starkebaum | 623/23.65 |
| 2004/0049269 A1 | * | 3/2004 | Corbitt et al. | 623/8 |
| 2004/0111004 A1 | * | 6/2004 | Loffler et al. | 600/7 |
| 2004/0225176 A1 | * | 11/2004 | Flanagan et al. | 600/7 |
| 2004/0260317 A1 | * | 12/2004 | Bloom et al. | 606/151 |
| 2005/0096497 A1 | * | 5/2005 | Gerber et al. | 600/30 |
| 2005/0113855 A1 | * | 5/2005 | Kennedy et al. | 606/185 |
| 2005/0216043 A1 | * | 9/2005 | Blatter et al. | 606/153 |
| 2005/0246037 A1 | * | 11/2005 | Starkebaum | 623/23.64 |
| 2005/0247320 A1 | * | 11/2005 | Stack et al. | 128/898 |
| 2005/0250973 A1 | * | 11/2005 | Ferguson | 600/8 |
| 2005/0261711 A1 | * | 11/2005 | Okada et al. | 606/153 |
| 2005/0261712 A1 | * | 11/2005 | Balbierz et al. | 606/153 |
| 2006/0058890 A1 | * | 3/2006 | Lesh | 623/23.72 |
| 2006/0063962 A1 | * | 3/2006 | Drobnik et al. | 600/7 |
| 2006/0079829 A1 | * | 4/2006 | Fulton et al. | 604/15 |
| 2006/0094929 A1 | * | 5/2006 | Tronnes | 600/104 |
| 2006/0287661 A1 | * | 12/2006 | Bolduc et al. | 606/153 |
| 2007/0021714 A1 | * | 1/2007 | Miller | 604/60 |
| 2007/0060932 A1 | * | 3/2007 | Stack et al. | 606/153 |
| 2007/0073322 A1 | * | 3/2007 | Mikkaichi et al. | 606/153 |
| 2007/0078291 A1 | * | 4/2007 | Terwilliger et al. | 600/7 |
| 2007/0093861 A1 | * | 4/2007 | Vardi | 606/153 |
| 2007/0129758 A1 | * | 6/2007 | Saadat | 606/232 |
| 2007/0162059 A1 | * | 7/2007 | Gannoe et al. | 606/153 |
| 2007/0208360 A1 | * | 9/2007 | Demarais et al. | 606/153 |
| 2008/0086155 A1 | * | 4/2008 | Rothe et al. | 606/153 |
| 2008/0147112 A1 | * | 6/2008 | Sheets et al. | 606/205 |
| 2008/0183195 A1 | * | 7/2008 | Baker | 606/153 |
| 2008/0221384 A1 | * | 9/2008 | Chi Sing et al. | 600/7 |
| 2009/0030260 A1 | * | 1/2009 | Mick | 600/7 |
| 2009/0125042 A1 | * | 5/2009 | Mouw | 606/153 |

| | | | |
|---|---|---|---|
| 2009/0187181 A1* | 7/2009 | Shadduck | 606/33 |
| 2009/0209984 A1* | 8/2009 | Swanstrom et al. | 606/153 |
| 2009/0270856 A1* | 10/2009 | Saadat et al. | 606/33 |
| 2009/0299125 A1* | 12/2009 | Wazer et al. | 600/7 |
| 2010/0113866 A1* | 5/2010 | Goldman | 600/30 |
| 2010/0179515 A1* | 7/2010 | Swain et al. | 604/543 |
| 2010/0204537 A1* | 8/2010 | Hermann et al. | 600/7 |
| 2010/0210892 A1* | 8/2010 | Lamoureaux et al. | 600/7 |
| 2010/0222641 A1* | 9/2010 | Chu et al. | 600/30 |
| 2010/0234670 A1* | 9/2010 | Shai et al. | 600/7 |
| 2010/0241028 A1* | 9/2010 | Johnson et al. | 600/567 |
| 2010/0256443 A1* | 10/2010 | Griguol | 600/30 |
| 2010/0256665 A1* | 10/2010 | Durgin | 606/191 |
| 2010/0256778 A1* | 10/2010 | Kennedy et al. | 623/23.72 |
| 2010/0261950 A1* | 10/2010 | Lund et al. | 600/30 |
| 2010/0318112 A1* | 12/2010 | Smith | 606/185 |
| 2010/0331874 A1* | 12/2010 | Bardy | 606/185 |
| 2011/0028779 A1* | 2/2011 | Chu | 600/30 |
| 2011/0124964 A1* | 5/2011 | Nobis | 600/129 |
| 2011/0152899 A1* | 6/2011 | Deem et al. | 606/153 |
| 2011/0171167 A1* | 7/2011 | Herring | 424/78.27 |
| 2011/0202078 A1* | 8/2011 | Kraemer et al. | 606/153 |
| 2011/0208219 A1* | 8/2011 | Pugsley et al. | 606/153 |
| 2011/0306820 A1* | 12/2011 | Witzmann | 600/30 |
| 2012/0065454 A1* | 3/2012 | Kader et al. | 600/8 |

FOREIGN PATENT DOCUMENTS

| | | |
|---|---|---|
| EP | 1 114 618 A2 | 7/2001 |
| JP | 09-268412 A | 10/1997 |
| WO | WO 95/16399 A1 | 6/1995 |
| WO | WO 01/28434 A1 | 4/2001 |
| WO | WO 02/13881 A1 | 2/2002 |
| WO | WO 02/060371 A1 | 8/2002 |

OTHER PUBLICATIONS

International Search Report completed Dec. 8, 2004 for International Application No. PCT/US2004/025777.

Written Opinion completed Dec. 8, 2004 for International Application No. PCT/US2004/025777.

International Preliminary Report on Patentability issued Feb. 13, 2006 for International Application No. PCT/US2004/025777.

* cited by examiner

FIG. 15
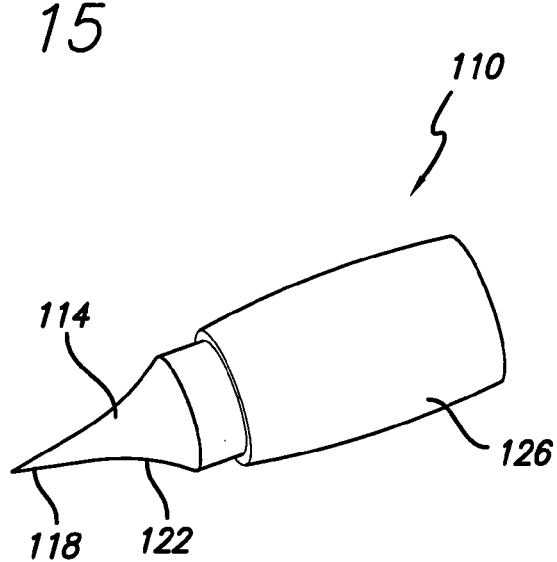
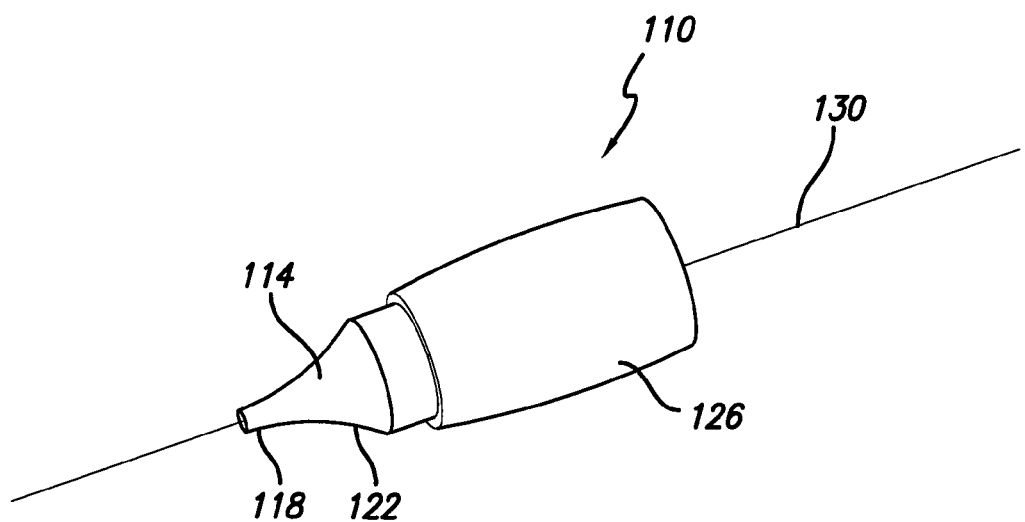
FIG. 16

SURGICAL IMPLANT

RELATED APPLICATIONS

This application is a continuation of U.S. application Ser. No. 10/915,626, filed Aug. 10, 2004, which claims the benefit of U.S. Provisional Application Ser. No. 60/494,613, entitled "Tipped Implant," filed on Aug. 11, 2003, and U.S. Provisional Application Ser. No. 60/558,163, entitled "Surgical Graft," filed on Mar. 31, 2004.

TECHNICAL FIELD

This invention relates to medical devices, and more particularly, to surgical implants.

BACKGROUND

Many surgical or endoscopic applications require the insertion of an implant into an incision in a patient's soft tissue. For example, such implants can be used to add bulk to a target tissue, thereby reinforcing the target tissue area. These procedures are often referred to as "bulking" procedures, and are frequently used in treating urological diseases, including urinary incontinence and vesicourethral reflux disease. "Bulking" procedures are also often used to treat Gastroesophageal Reflux Disease (hereinafter "GERD"). GERD is a form of dyspepsia that afflicts approximately 40% of adults in the United States. More specifically, GERD is a pathophysiologic condition of the esophagus in which gastric fluids escape from the stomach and travel into the esophagus. The symptoms of GERD can include heartburn, regurgitation of gastric contents, or dysphagia, which is a difficulty in swallowing or moving swallowed material into the stomach. GERD often results from, among other things, transient lower esophageal sphincter (hereinafter "LES") relaxations and decreased LES resting tone.

One endoscopic procedure used to treat GERD involves transmurally inserting one or more implants into preformed incisions in the LES, and particularly into the submucosal tissue layer, as described in U.S. Pat. No. 6,098,629 to Johnson et al., which is fully incorporated herein by reference. In general, the implants effectively treat GERD by increasing the mass of the LES, thus improving the LES resting tone. The procedure involves first endoscopically identifying an insertion site to access the submucosa adjacent the LES. The layer of mucosa that covers the submucosa is then pierced by a sharp dissection tool. Next, a pouch sized to receive the prosthesis is created in the submucosa. The pouch can be created by liquid infusion (i.e., by forming a blister) or by blunt dissection using a blunt tool. Once the pouch is created, the implant is inserted into the pouch. The implant is typically inserted by a grasper, a clamshell deployment device, or another similar insertion tool. After insertion, the mucosal opening is closed by using an appropriate conventional closing technique.

Soft tissue implants can also be used for brachytherapy. Brachytherapy involves inserting a radioactive implant directly into or adjacent a tumor to effect remission of the tumor. Similarly, soft tissue implants can be used to deliver various drugs to a target location. That is, once an implant impregnated or coated with a drug is implanted in a patient's soft tissue, the implant releases the drug into the patient.

However, presently available procedures for inserting an implant have several significant drawbacks, including implant migration. Implants migrate when, for example, the pouch created to accommodate the implant is too large for the implant. In this situation, the implant can be displaced from its target position into a less ideal position. In more serious cases, implant migration renders the implant entirely ineffective, thus requiring follow-up or additional medical procedures.

Another drawback is the size of presently available implants. Often times a single implant is simply too small to achieve the desired bulk in the target area. Thus, the insertion of multiple implants in the target area is often required. Delivering multiple implants, however, can require that a physician reinsert the delivery tool into a target tissue for each implant, thus increasing the time required for the procedure and causing unnecessary trauma.

Presently available procedures for transmurally inserting an implant, for example, into the LES, have several additional drawbacks. First, creating a pouch for the implant typically causes excessive trauma to the surrounding tissues, especially if a blunt tool is used to create the pouch. Another drawback is that insertion of an implant into the target tissue can be difficult because the implant can catch or snag on the edges of the mucosal incision. Moreover, implants can be difficult to deliver into a target tissue along a desired trajectory and in a desired spatial orientation.

BRIEF SUMMARY

Accordingly, it is an object of the present invention to provide a medical device having features that resolve or improve upon one or more of the above-described drawbacks.

According to a first aspect of the present invention, the foregoing object of the present invention is obtained by providing a linked implant having two or more bio-remodelable implant bodies disposed along a length of string. The implant bodies can be formed of an extra-cellular matrix material, such as small intestine submucosa, and can be shaped as desired for a given application. For example, the implant bodies can be spherical, ellipsoid, cuboid, or cylindrical in shape. Additionally, radiopaque markers can be provided to assist in visualization of the device during delivery within a patient. According to another aspect of the present invention, the foregoing object is obtained by providing a linked implant that forms a net or matrix. According to yet another aspect of the present invention, methods are provided for assembling a linked implant.

According to yet another aspect of the present invention, the foregoing object of the present invention is obtained by providing a tipped implant including an implant body having a first outside periphery, and a penetrating member connected to the implant body. The penetrating member can be formed from a biocompatible material such as stainless steel, plastic, or even a rigid bio-resorbable material. The penetrating member includes a penetrating portion and an expanding portion located adjacent to the penetrating portion. The penetrating portion can form a leading edge or a leading point. The expansion portion expands the opening created by the penetrating portion to a diameter that is sufficiently large to receive the implant.

According to another aspect of the present invention, a passageway that extends axially through the implant body and/or the penetrating member can be provided. The passageway permits the tipped implant to be directed over a guidewire to the target site.

According to another aspect of the present invention, a method is provided for assembling a tipped implant. According to yet another aspect of the invention, a method is provided for simultaneously creating an opening sized to receive an implant and inserting the implant into the opening.

BRIEF DESCRIPTION OF THE DRAWINGS

FIG. 15 is a perspective side view of one embodiment of the present invention including an implant and an implant tip;

FIG. 16 is a perspective side view of one embodiment of the present invention including an implant, an implant tip, a channel, and a guidewire;

DETAILED DESCRIPTION OF THE PRESENTLY PREFERRED EMBODIMENTS

Figure 1:
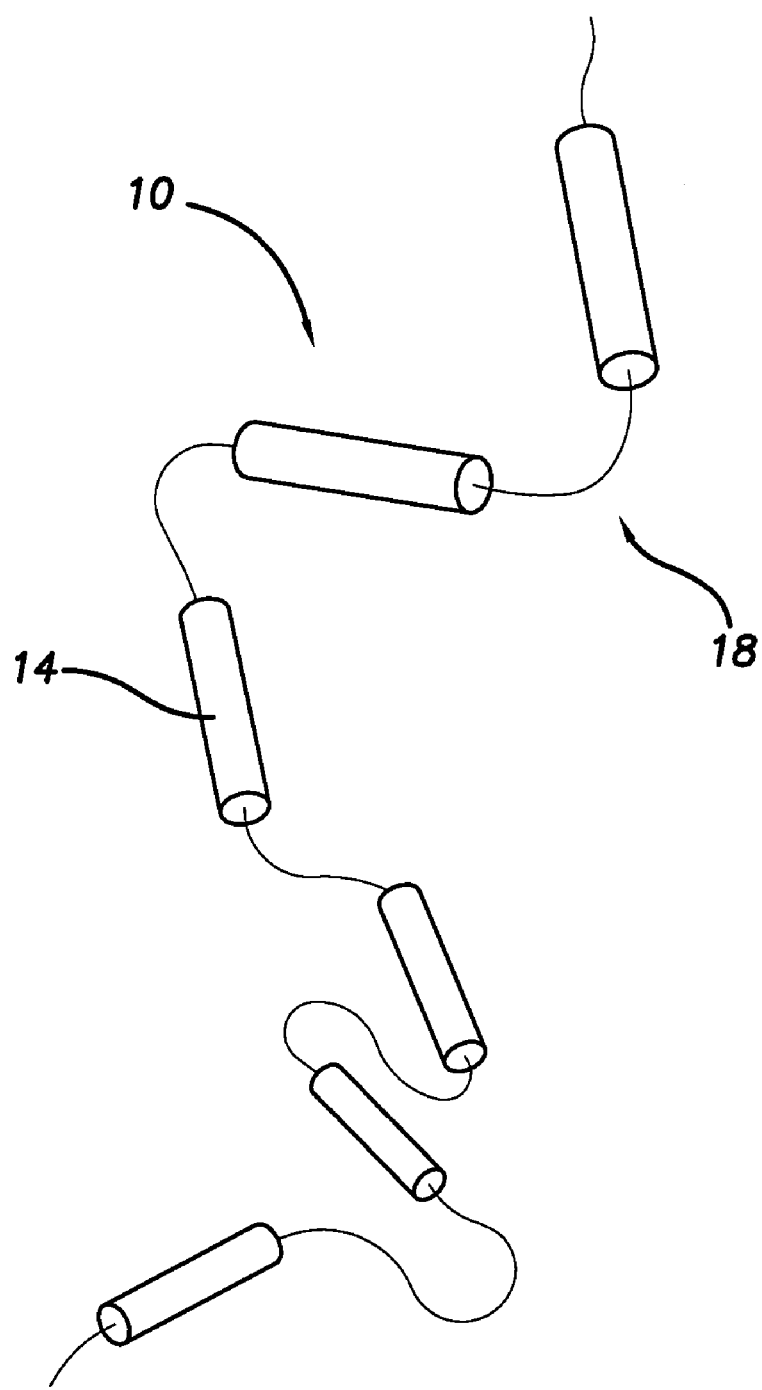
FIG. 1 is a side view of one embodiment of the present invention including several cylindrical implant bodies and a string.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances, details which are not necessary for an understanding of the present invention, such as conventional details of fabrication and assembly, have been omitted.

Referring to the drawings, FIG. 1 illustrates a first embodiment of the present invention, and particularly, linked implant 10. As illustrated in FIGS. 1-4, linked implant 10 normally comprises two or more implant bodies 14 attached to a string 18. In general, linked implant 10 is delivered to a location adjacent the target tissue (e.g., the esophageal lumen, superior to the LES). Linked implant 10 is then introduced into the target tissue, thereby bulking the surrounding tissue.

Implant body 14 can be formed of a variety of desirable, biocompatible implant materials suitable for bulking and supporting a target tissue. In a preferred embodiment of the present invention, the implant body is formed of a bio-remodelable, extra-cellular matrix. One suitable form of extra-cellular matrix is harvested from porcine or bovine small intestine submucosa (hereinafter "SIS"). SIS is a preferred material because it has special bio-remodeling characteristics. Because of these characteristics, SIS has been used successfully in various surgical applications. One such application is described in U.S. Pat. No. 6,358,284 to Fearnot et al., which is incorporated herein by reference. That surgical application involves the application of purified submucosa as a ureter graft. As an alternative to using a bio-remodelable material such as SIS, the implant body can be formed from a variety of other bio-compatible materials, including for example, stainless steel, polymers, and biocompatible foams such as silicone foam or polyurethane foam.

Figure 2:
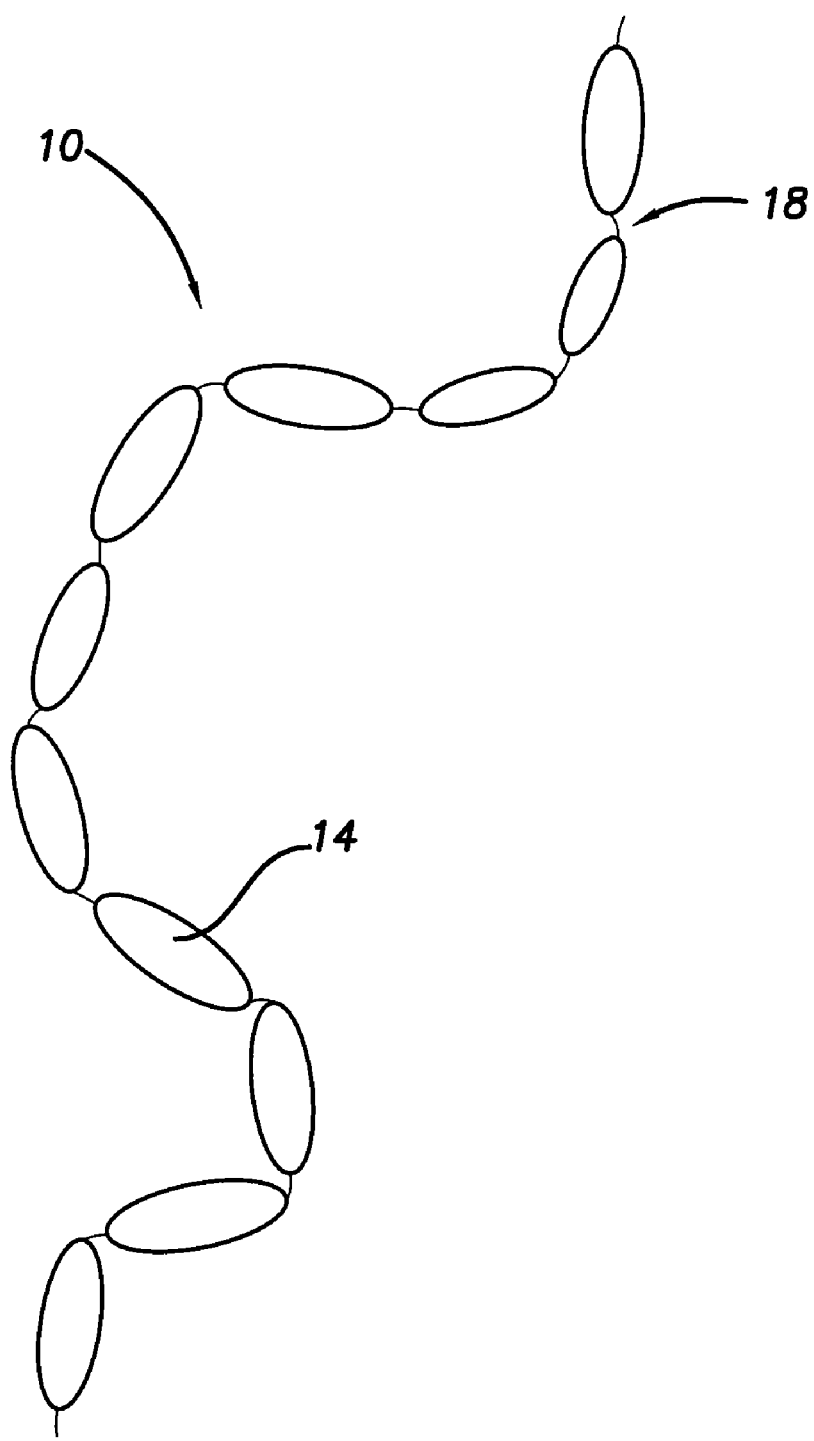
FIG. 2 is a side view of one embodiment of the present invention including several ellipsoid implant bodies and a string.
Figure 3:
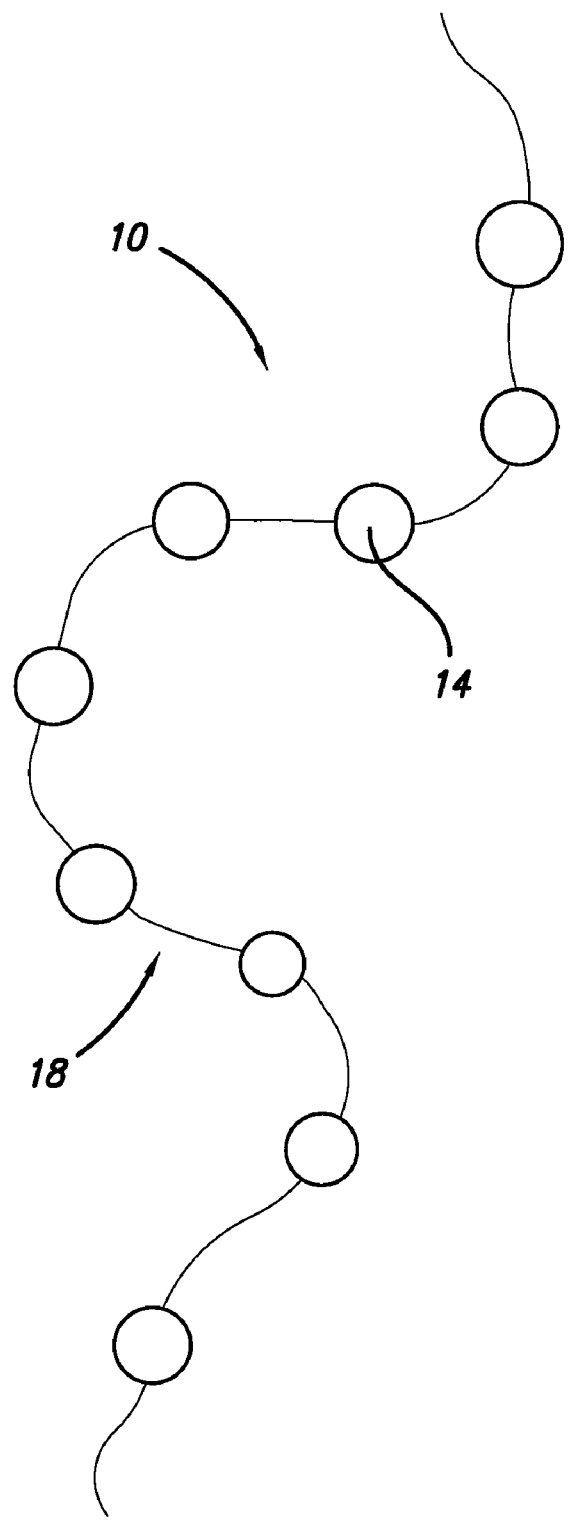
FIG. 3 is a side view of one embodiment of the present invention including several spherical implant bodies and a string.
Figure 4:
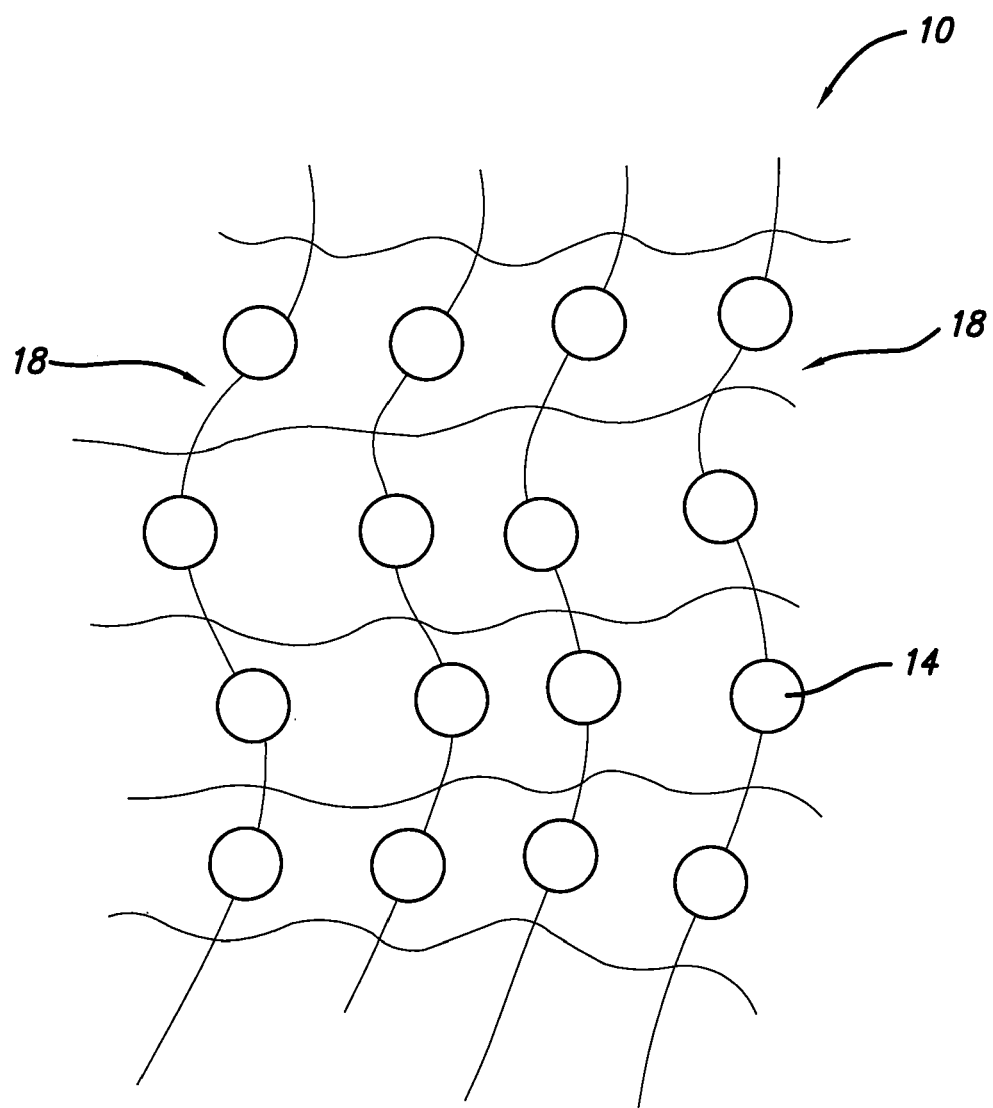
FIG. 4 is a side view of one embodiment of the present invention including a bulking net.

As shown in FIGS. 1-4, the implant bodies 14 can be provided in a wide variety of shapes. For example, implant bodies 14 can be formed into cylindrical bodies (FIG. 1), ellipsoid bodies (FIG. 2) or spherical bodies (FIGS. 3 and 4). Likewise, the size of each implant body can vary depending on the particular medical application for the linked implant. Moreover, depending on the therapeutic needs of a patient, e.g., treatment of a tumor, the implant body also can be impregnated or covered with a drug suitable for causing the desired therapeutic outcome.

Figure 5:
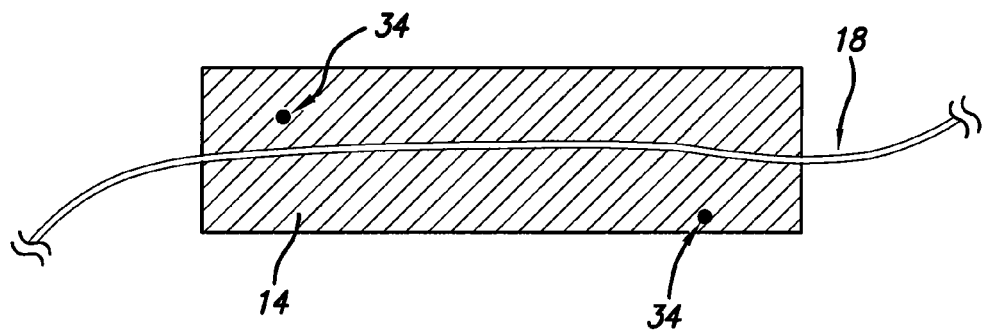
FIG. 5 is a cross-sectional side view of one embodiment of the present invention including radiopaque markers.

As shown in FIG. 5, a biocompatible, radio-opaque powder, ball, or other marker, for example stainless steel ball 34, can also be added to the implant body. As a result, a physician can track the position of the implant body relative to the surrounding anatomy and/or the target tissue, thereby facilitating proper placement of the linked implant within the patient. For example, the physician can track the position of the implant body fluoroscopically during the delivery of the linked implant.

As illustrated in FIGS. 1-5, linked implant 10 includes a string 18 that is used to link two or more implant bodies 14. Once properly placed in a target tissue, string 18 secures and stabilizes implant bodies 14. In particular, string 18 prevents implant bodies 14 from individually migrating into an undesired or ineffective position. String 18 can be a biocompatible mono-filament or thread. One preferred material is the thread or filament utilized in resorbable sutures. Alternatively, non-resorbable sutures can be used.

It should also be noted that implant bodies 14 can be disposed closely together, as shown in FIG. 2, or spread apart from each other, as shown in FIGS. 1, 3, and 4. That is, the separation between implant bodies can be tailored to a particular desired position along the string or filament. Further, the implant bodies need not be disposed along the string equidistantly. Rather, the distances between adjacent implant bodies can by varied as desired. Moreover, as illustrated in FIG. 4, implant bodies 14 can be disposed on a net of filaments. Such a net arrangement allows a physician to extend the implants laterally and longitudinally relative to a wound or surgical site, thus reinforcing and bulking the wound or surgical site.

Figure 6:
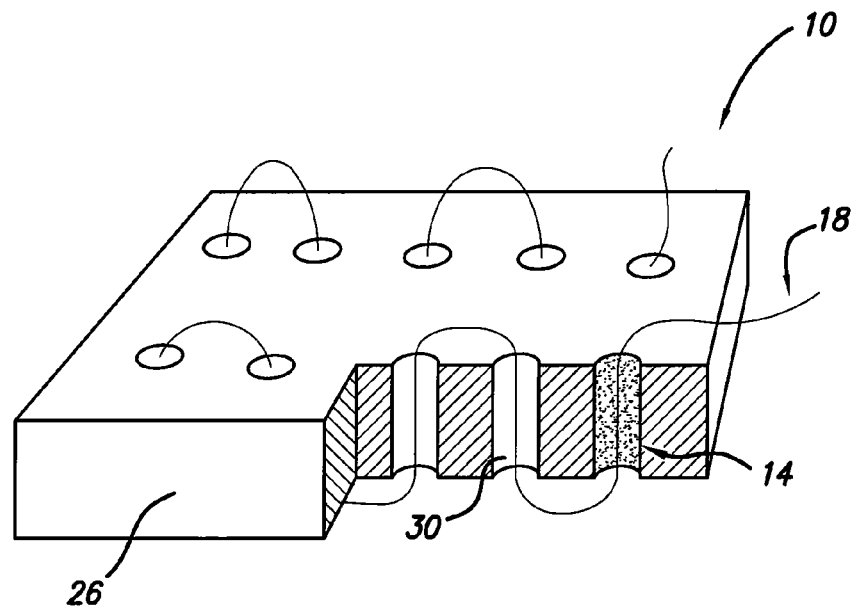
FIG. 6 is a cross-sectional side view of one embodiment of the present invention including an assembly mold.

A variety of methods can be employed to assemble linked implant 10. A preferred method of assembly is illustrated in FIG. 6. Mold 26 is configured to form cylindrical implant bodies 14. A mold capable of forming spherical, cuboid, and/or elliptical implant bodies could alternatively be used. While illustrative mold 26 is configured to form a linked implant 10 having ten (10) implant bodies 14, molds capable of forming a linked implant with additional or fewer implant bodies could be used.

Linked implant 10 is assembled as illustrated in FIG. 6. First, a string 18 is threaded through cylindrical forms 30. After string 18 is in place, the desired implant material is packed into each cylindrical form 30. In one method, the implant material comprises a liquid that is injected into the form. Before cylindrical form 30 has been completely filled with the implant material, such as SIS, a radio-opaque marker 34 can be optionally inserted into the cylinder. Once the linked implant is assembled, it is dried. The linked implant can be air-dried or freeze-dried, preferably overnight. The dried, linked implant can then be removed from mold 26 and cut to a desired length with a scalpel or scissors. It should be noted that alternative curing methods can be used for various materials. For example, linked implants formed of epoxy materials are cured through polymerization or cross-linking reactions, and linked implants formed of cement materials are cured through hydrolysis reactions. Additional exemplary methods of forming a linked implant include insert molding, wherein a plastic can be injected into a molding and an additional object can be inserted into the plastic.

Figure 14:
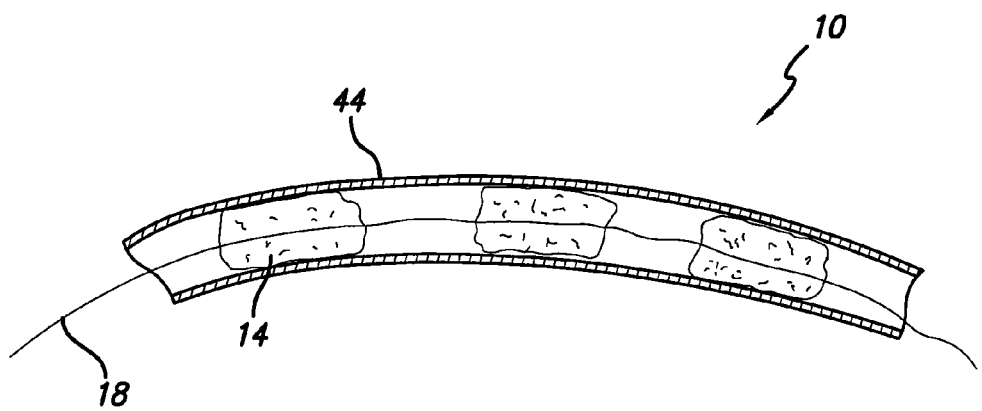
FIG. 14 is a cross-sectional side view of one embodiment of the present invention including an assembly tube.

Linked implant 10 can also be assembled as illustrated in FIG. 14. FIG. 14 illustrates a tubular mold used to assemble implant bodies 14 and string 18. To assemble linked implant 10, the desired implant material is packed into tubular mold 44. The linked implant can be air-dried or freeze-dried, preferably overnight. The dried, linked implant 10 can then be removed from tubular mold 44 and cut to a desired length with a scalpel or scissors.

Figure 7:
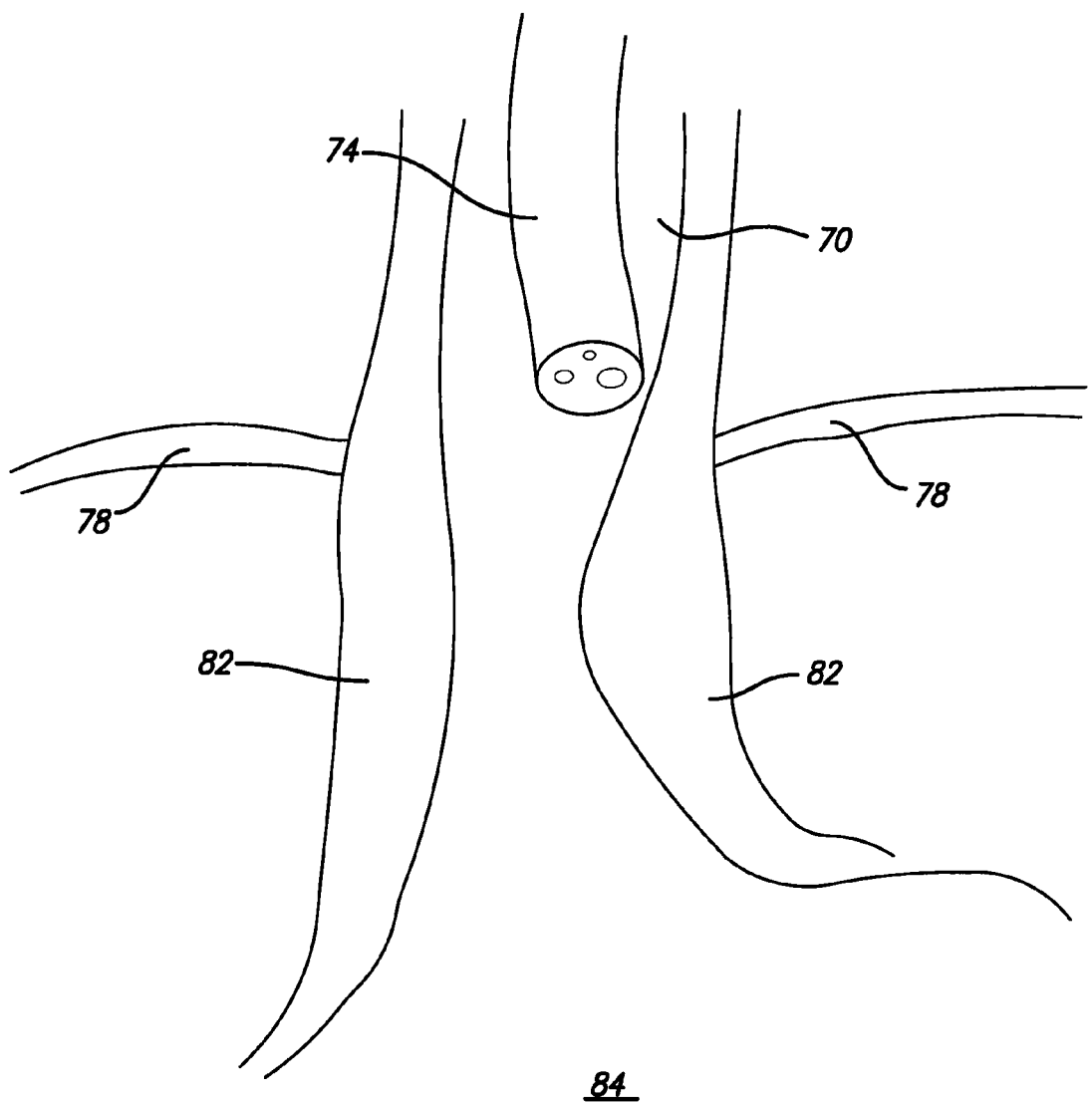
FIG. 7-12 sequentially illustrate a method of inserting a linked surgical implant according to one embodiment of the present invention.
Figure 8:
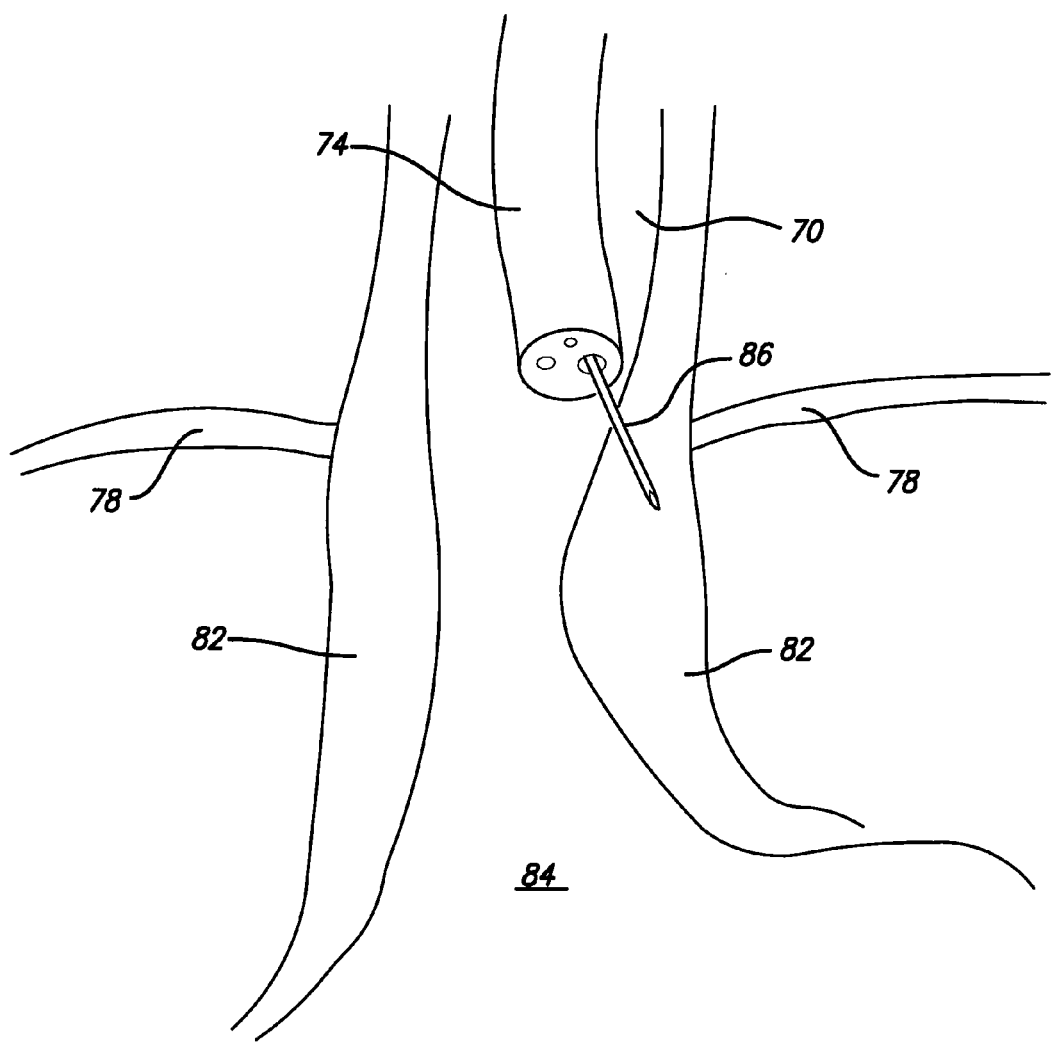
Figure 9:
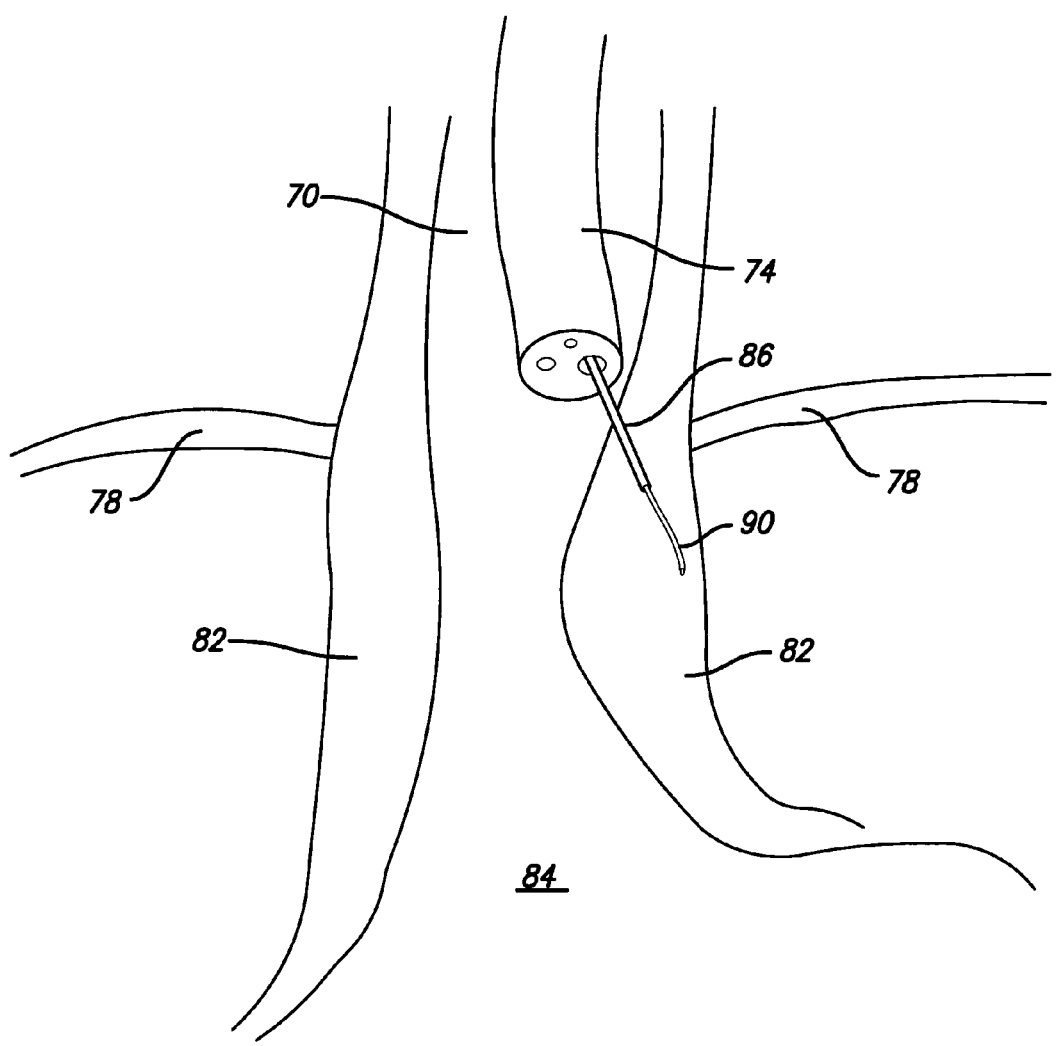
Figure 10:
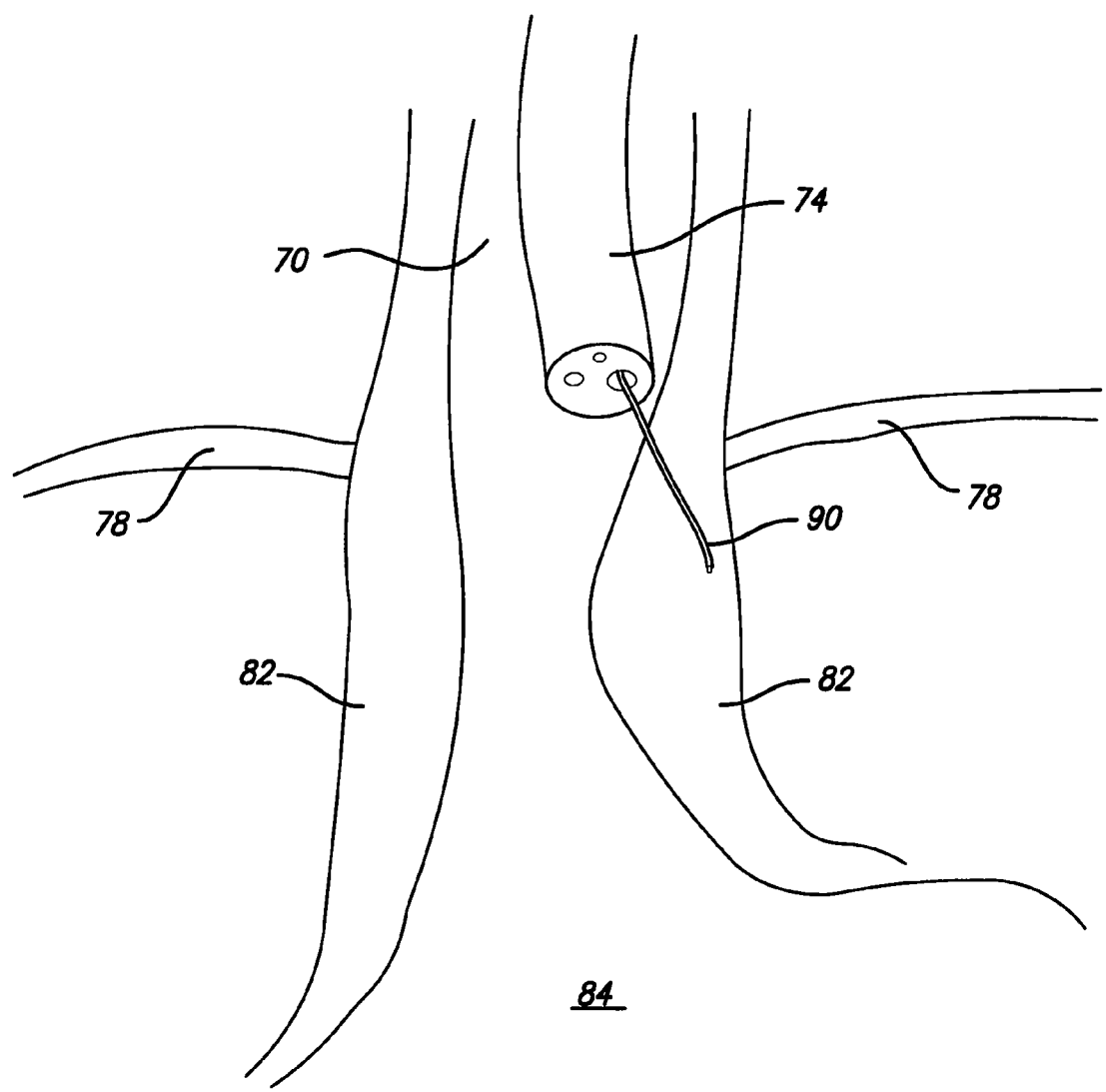
Figure 11:
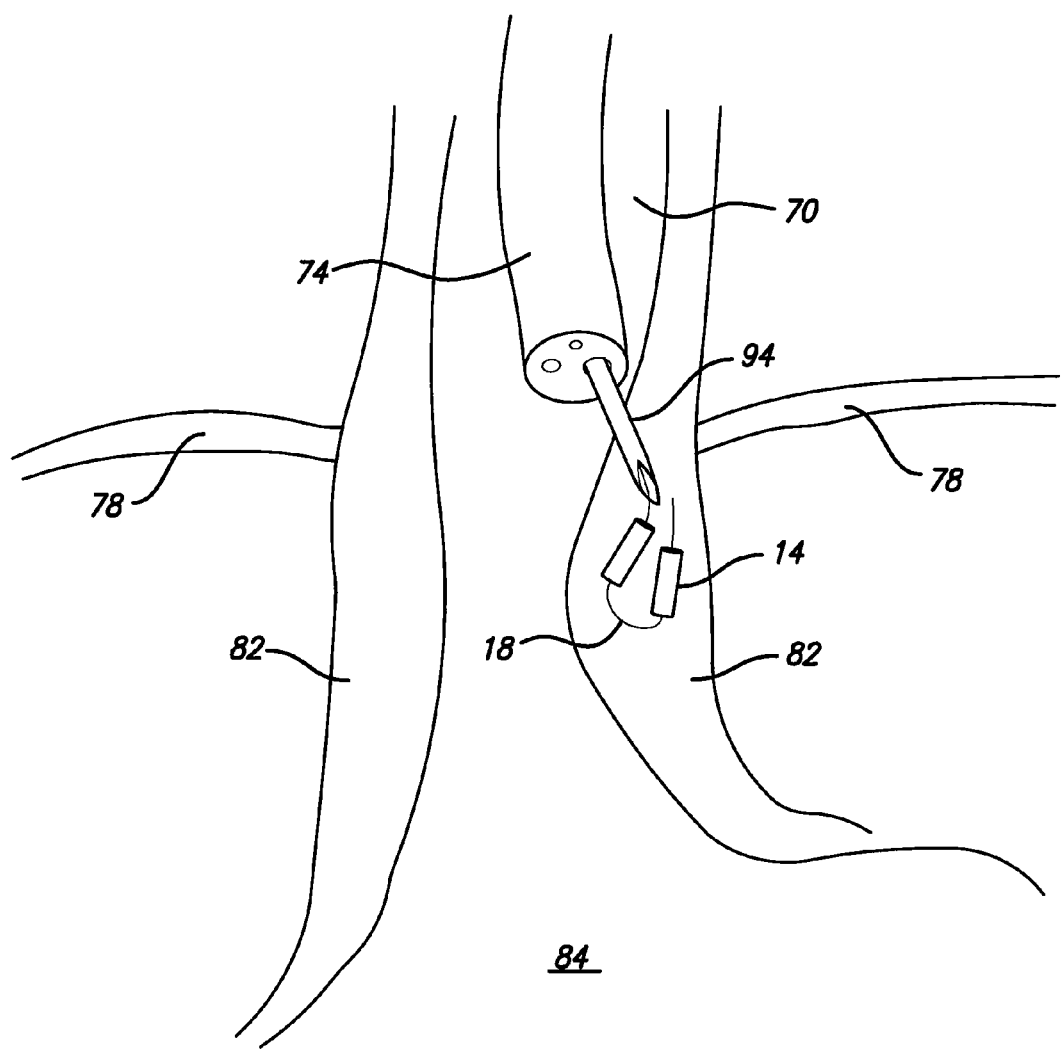
Figure 12:
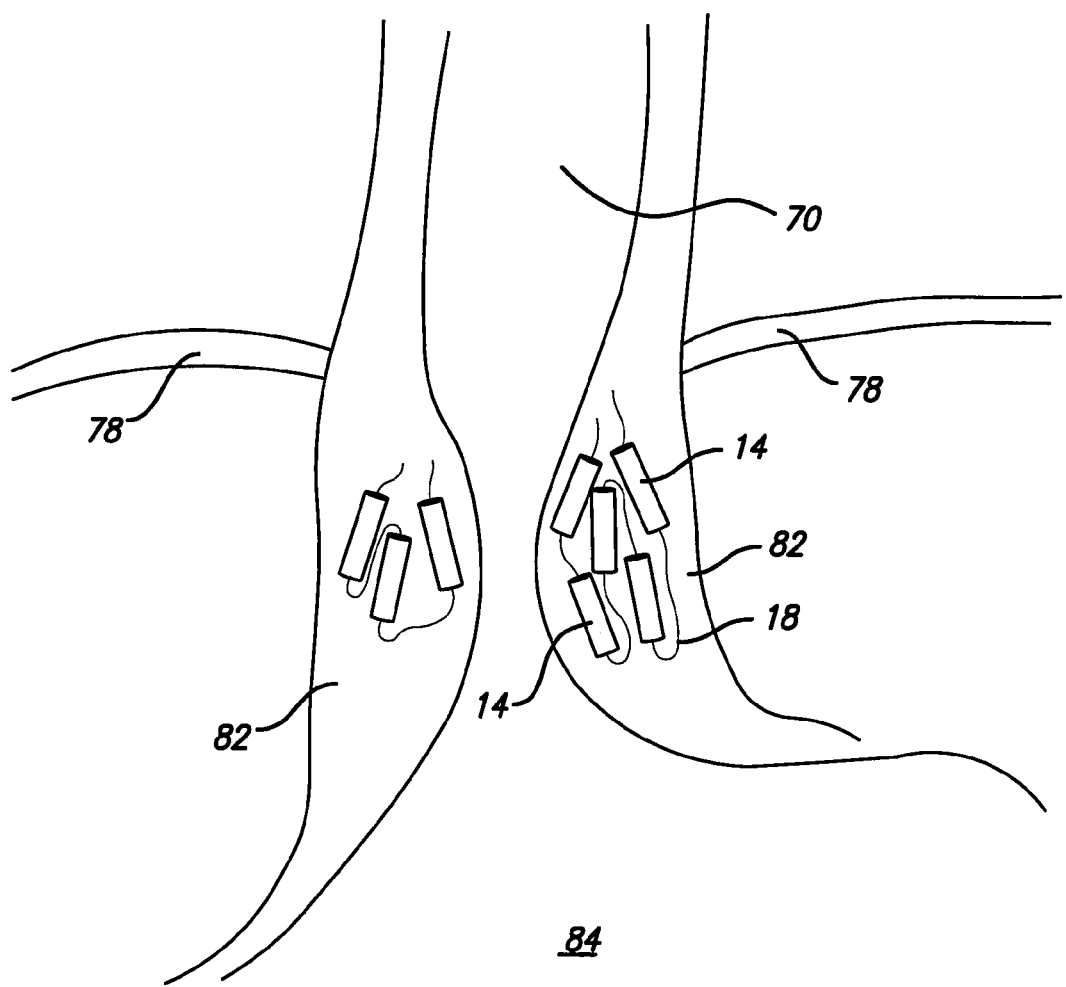

Linked implant 10 can be used for a wide variety of applications, including minimally invasive or open surgical applications. An exemplary minimally invasive procedure is the treatment of GERD by bulking the LES. For applications involving GERD, a preferred method of delivering the linked implant generally includes first identifying the desired implant location with an endoscope and then inserting the linked implant into that location. Referring to FIG. 7, an illustrative endoscope 74 (which is preferably an X-Ray fluoroscope, ultrasound endoscope, or conventional endoscope) is passed through the mouth and esophagus 70 of a patient and delivered to the vicinity of LES 82, superior to the stomach 84 and adjacent to diaphragm 78. A needle 86 is passed through the working channel of endoscope 74 and into the LES 82, as shown in FIG. 8. As illustrated in FIG. 9, once needle 86 is in the LES 82, guidewire 90 is inserted to maintain access to the target tissue. Needle 86 is withdrawn, while guidewire 90 remains in the target tissue, as illustrated in FIG. 10. Subsequently, catheter 94 is inserted over the guidewire and into the desired implant location to deliver linked implant 10, as shown in FIG. 11. Linked implant 10 can be pushed into the LES by a conventional pusher tool inserted through the lumen of the catheter 94 (FIG. 11) into the desired implant location. As illustrated in FIG. 11, throughout the delivery of the linked implant, the position of catheter 94 can be changed to distribute additional implant bodies 14 throughout the target tissue area. Once the linked implant is in the target tissue, catheter 94 and endoscope 74 are withdrawn, as illustrated in FIG. 12.

Figure 13:
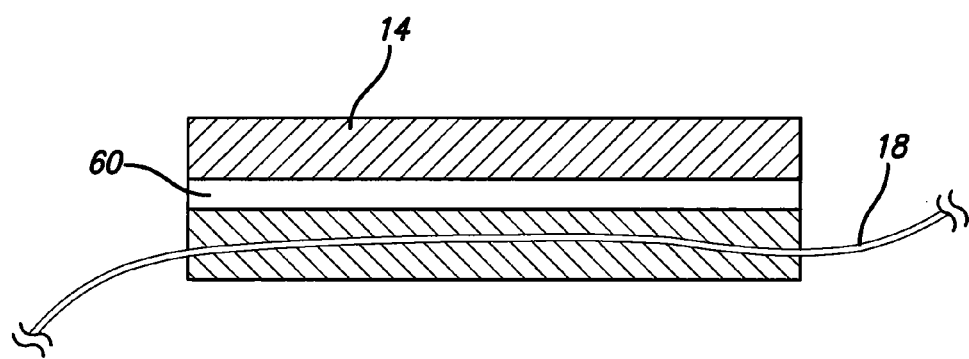
FIG. 13 is a cross-sectional side view of one embodiment of the present invention including a guidewire lumen.

As shown in FIG. 13, the linked implant can alternatively be configured for delivery directly over a guidewire. In this delivery configuration, the implant body 14 is provided with a passageway 60, which is adapted to receive a guidewire. Before delivery, a plurality of implant bodies 14 are back-loaded onto a guidewire. Once the implant bodies are loaded, the distal end of the guidewire can be inserted into the target tissue, as shown in FIG. 10. A conventional pusher tool (not shown) is then used to push the implant bodies into the target tissue.

It should also be noted that the linked implant can alternatively be delivered without the use of a guidewire. For example, the linked implant can be delivered into a target tissue through a catheter inserted directly into the LES. In another alternative, a cannula can be used to deliver the linked implant.

Linked implant 10 can alternatively be used in various open surgical procedures in which tissue bulking or reinforcement is necessary. Linked implant 10 can be directly inserted into an incision by a physician. In either open or minimally invasive procedures, the physician can tailor the linked implant 14 for the particular incision by, for example, using several separate linked implants, joining two or more linked implants to increase overall implant length, or cutting a linked implant to reduce its overall length. Alternatively, a physician can insert a net of interconnected linked implants (see FIG. 4). Indeed, a physician can wad or bundle the net of interconnected linked implants and insert the wadded or bundled net into an incision. A net configuration can be particularly useful where a physician desires to reinforce or bulk a large incision.

Figure 17:
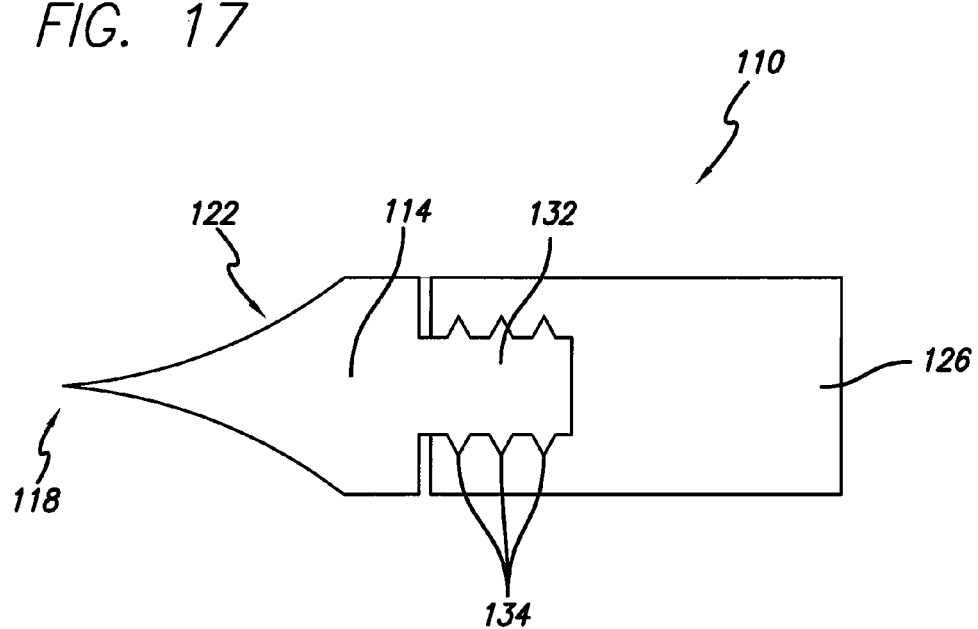
FIG. 17 is a cross-sectional side view of one embodiment of the present invention including an implant, and an implant tip.

Referring to the drawings, FIGS. 15 and 16 illustrate a second embodiment of the present invention, and particularly, tipped implant 110. As best seen in FIG. 15, tipped implant 110 generally comprises implant body 126 (often having a rough or non-uniform edge), and a smooth implant tip 114 having a penetrating portion and an expanding portion. As illustrated in FIG. 17, tip 114 also includes a proximal end having shank 132 with threads 134. As discussed in greater detail below, shank 132 secures implant body 126 to tip 114.

In general, tipped implant 110 is delivered to a location adjacent the target tissue (e.g., the esophageal lumen, superior to the LES) through the working channel of an endoscope. Tip 114 is then introduced into the target tissue such that the penetrating portion of the tip punctures the target tissue. As the tip is advanced into the target tissue, the expansion portion of the tip widens the puncture created by the penetrating portion, thus forming a cavity sized to receive the tipped implant. Additionally, the shape of the tip is preferably configured to control or guide the orientation and trajectory of the implant body as the tip penetrates and enters the target tissue. That is, the tip can be configured to dilate the target tissue as necessary to achieve a desired orientation and trajectory for the implant body. For example, the tip can be curved, thereby guiding the implant body over a curved trajectory as the implant body enters the target tissue. Alternatively, the tip can be formed to simply puncture and/or dilate a target tissue.

As best illustrated in FIG. 15, tip 114 comprises a distal end having a penetrating portion or point 118. The leading point of the tip is preferably sharp so as to easily pierce or puncture the target tissue while avoiding unnecessary trauma to adjacent tissues. Of course, in alternative embodiments of the present invention, the penetrating portion can be formed into a variety of shapes configured to penetrate, cut, tear, stretch, or otherwise dilate the target tissue. Alternatively, the penetrating portion can be provided with a cutting edge to further facilitate penetration of the tipped implant into a target tissue. For example, a wedge-shaped tip having a sharpened leading edge can be used. As illustrated in FIG. 15, tip 114 has a round cross-section. However, other shapes having different cross-sections can alternatively be used. For example, the tip can be triangular, square, elliptical, or otherwise asymmetrical in cross section.

The tip can be formed of a variety of materials that are sufficiently rigid to penetrate the target tissue. For example, the tip can be formed of metals, ceramics, polymers, composites, natural materials, bio-resorbable materials, or dissolvable materials. In a preferred embodiment of the present invention the implant tip is formed from surgical grade stainless steel.

As best illustrated in FIG. 15, tip 114 also includes an expanding portion 122. Expanding portion 122 is adapted to enlarge the puncture the incision initially created by point 118 to a shape that closely approximates the projected shape of the tipped implant. As shown in FIGS. 15 and 17, expanding portion 122 is funnel-shaped so as to reduce trauma to the dilated tissue. Additionally, as illustrated in FIG. 15, the maximum circumference of expanding portion 122 is preferably about the same size as or slightly larger than implant body 126. This ensures that the opening created by the tip is large enough so that the implant body does not catch or snag on the tissue surrounding the opening. Alternatively, the expanding portion can be configured to expand the opening created by point 118 to a circumference that is significantly larger than the circumference of the implant body. The expanding portion of the tip can also be configured to resist migration of the tipped implant 110 in an undesirable direction. This can be accomplished by the addition of an arrow-shaped or lanciform expanding portion that readily penetrates and expands the target tissue as the tipped implant is moved in a first direction, yet resists movement in a second direction opposite the first direction.

Tip 114 further includes shank 132, as illustrated in FIG. 17. Shank 132 is located at the proximal end of tip 114, and is adapted to secure tip 114 to implant body 126. In addition, threads 134 are provided as a gripping surface to securely fasten implant body 126 to tip 114. Implant body 126 is fastened to shank 132 and abuts the proximal end of the tip, as described in detail below.

Figure 18:
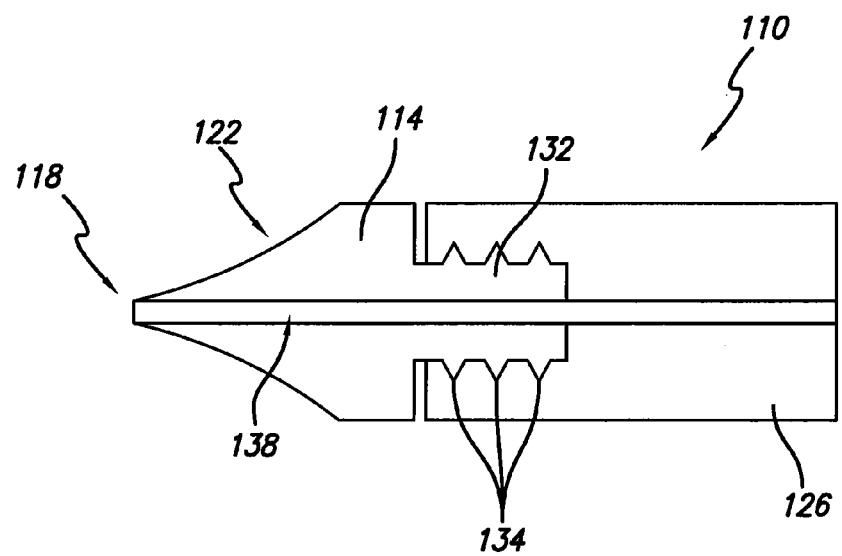
FIG. 18 is a cross-sectional side view of one embodiment of the present invention including an implant, an implant tip, and a channel.
Figure 19:
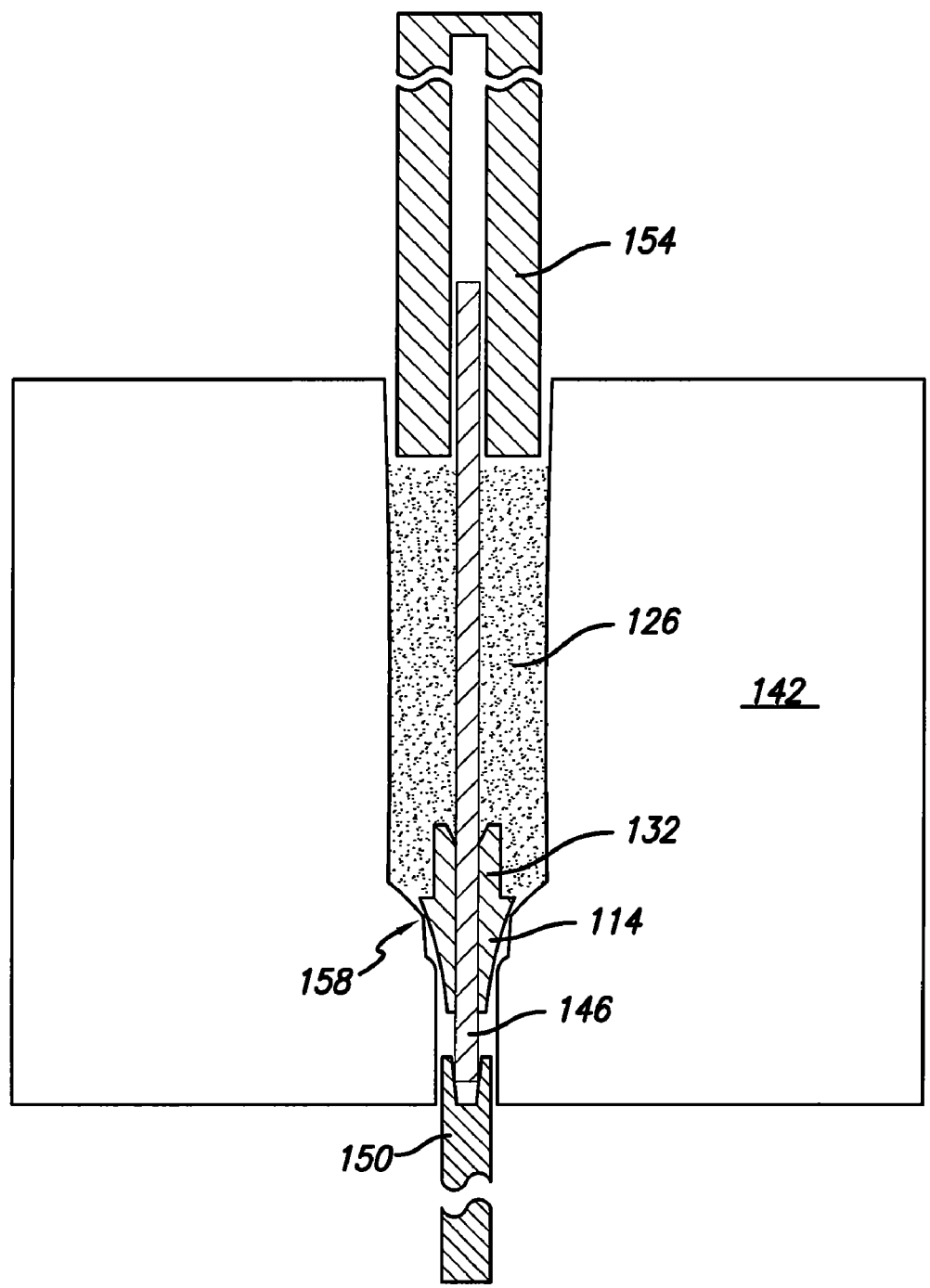
FIG. 19 is a cross-sectional side view of one embodiment of the present invention including an assembly mold.
Figure 20:
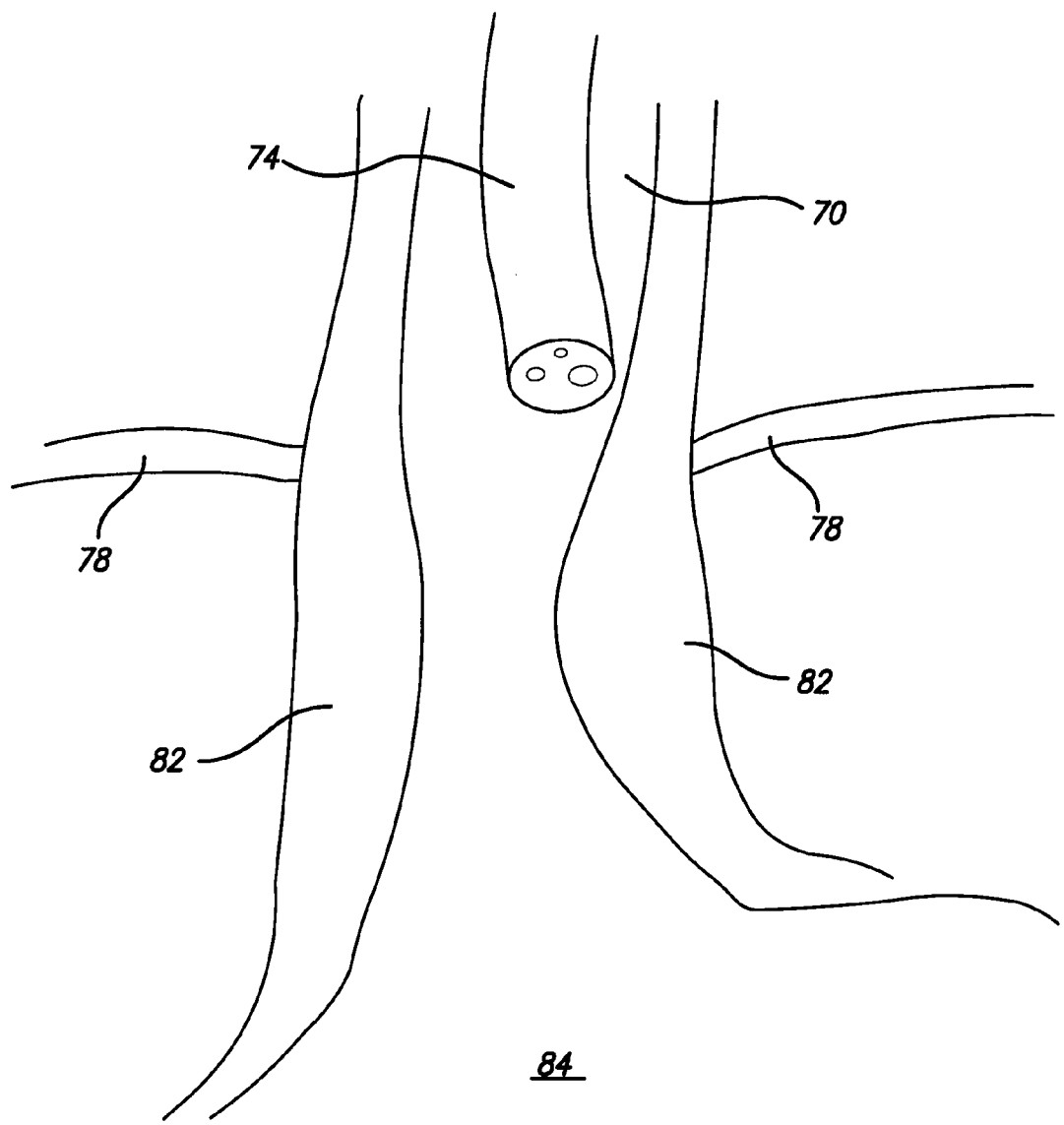
FIGS. 20-26 sequentially illustrate one embodiment of the method according to the present invention to implant a medical device having an implant with an implant tip.

In a third embodiment of the present invention, shown in FIGS. 16, 18 and 19, medical device 110 is provided with passageway 138. Passageway 138 extends axially through both tip 114 and implant body 126. Passageway 138 is adapted to slide over a guidewire, needle, or a cannula. The tip of the tipped implant 110 can therefore be inserted into the target tissue with the proper orientation relative to the target tissue. As a result, passageway 138 facilitates insertion of tipped implant 110. When the medical device is used in conjunction with a catheter, needle, or cannula, the target tissue can easily be pierced and infused with a desired fluid before insertion of the medical device. Other than the inclusion of passageway 138, the third embodiment of the tipped implant 110 is the same as the second embodiment described above.

The implant body 126 can be formed of a variety of desirable implant materials, such as those discussed with respect to the implant bodies of the first embodiment. As noted above, in a preferred embodiment of the present invention, the implant body is formed of purified submucosa, which is a bio-remodelable material that can be derived from, among other things, the small intestine submucosa of vertebrates. A biocompatible, radio-opaque powder or other marker can also be added to the implant body. This facilitates proper placement of the tipped implant within the patient.

A variety of methods can be employed to assemble tipped implant 110. A preferred method of assembly includes securing the distal end of the tip, either manually or by a clamp. A rod is then inserted through the tip passageway. Thin strips of SIS are coiled around the shank and the rod as necessary to create an implant body having a desired diameter. Once the tipped implant is assembled, it is dried. The tipped implant can be air-dried or freeze-dried, preferably overnight. The dried implant body can then be cut to a desired size with a scalpel.

Another method of assembly is illustrated in FIG. 19 and involves tamping strips of SIS material into a mold that grips the implant tip. In this particular method, a rod 146 is first inserted through tip 114. An end of a strip of SIS material is then temporarily pinned to shank 132 (for example, by pressing the end of the strip to shank 132) and the remainder of the strip of SIS is loosely wrapped around shank 132 and a proximal portion of rod 146. Tip 114 is thereafter inserted into mold 142 far enough so that tip 114 engages and is retained by edge 158 of mold 142. Once the tip and strip of SIS are inserted into mold 142, packing rod 154 is used to tamp the strip, or strips, of SIS to shank 132. The tip and strip of SIS is then dried in the mold, as described above with respect to the manually assembled implant. After the implant is dried in the mold, pusher rod 150 is used to remove the assembled implant body and tip from mold 142. As necessary, additional strips of SIS can be added to the tip by repeating the same process. Notably, drying the implant in the mold results in a smooth, low-profile implant that can be implanted more smoothly.

Figure 21:
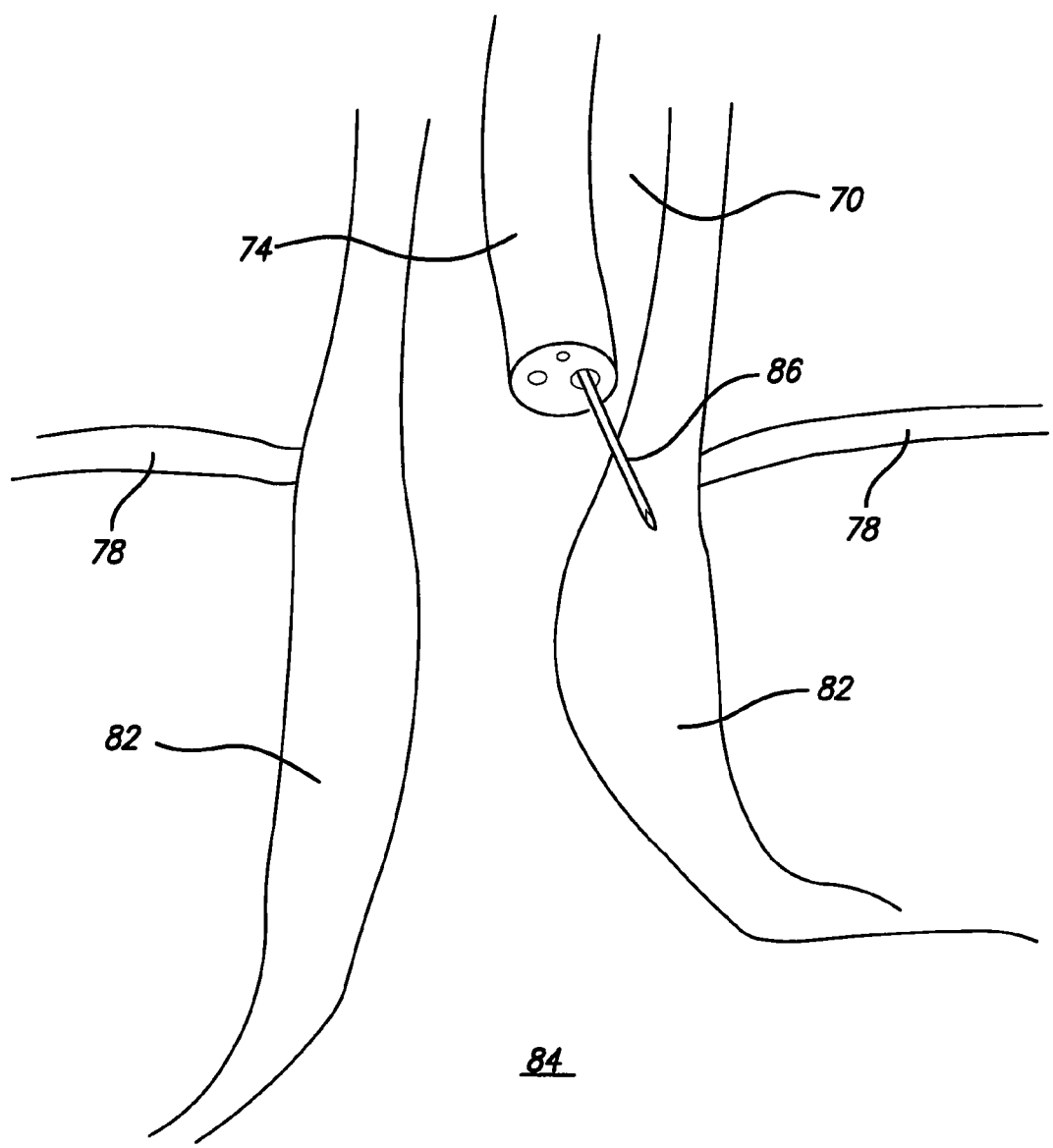
Figure 22:
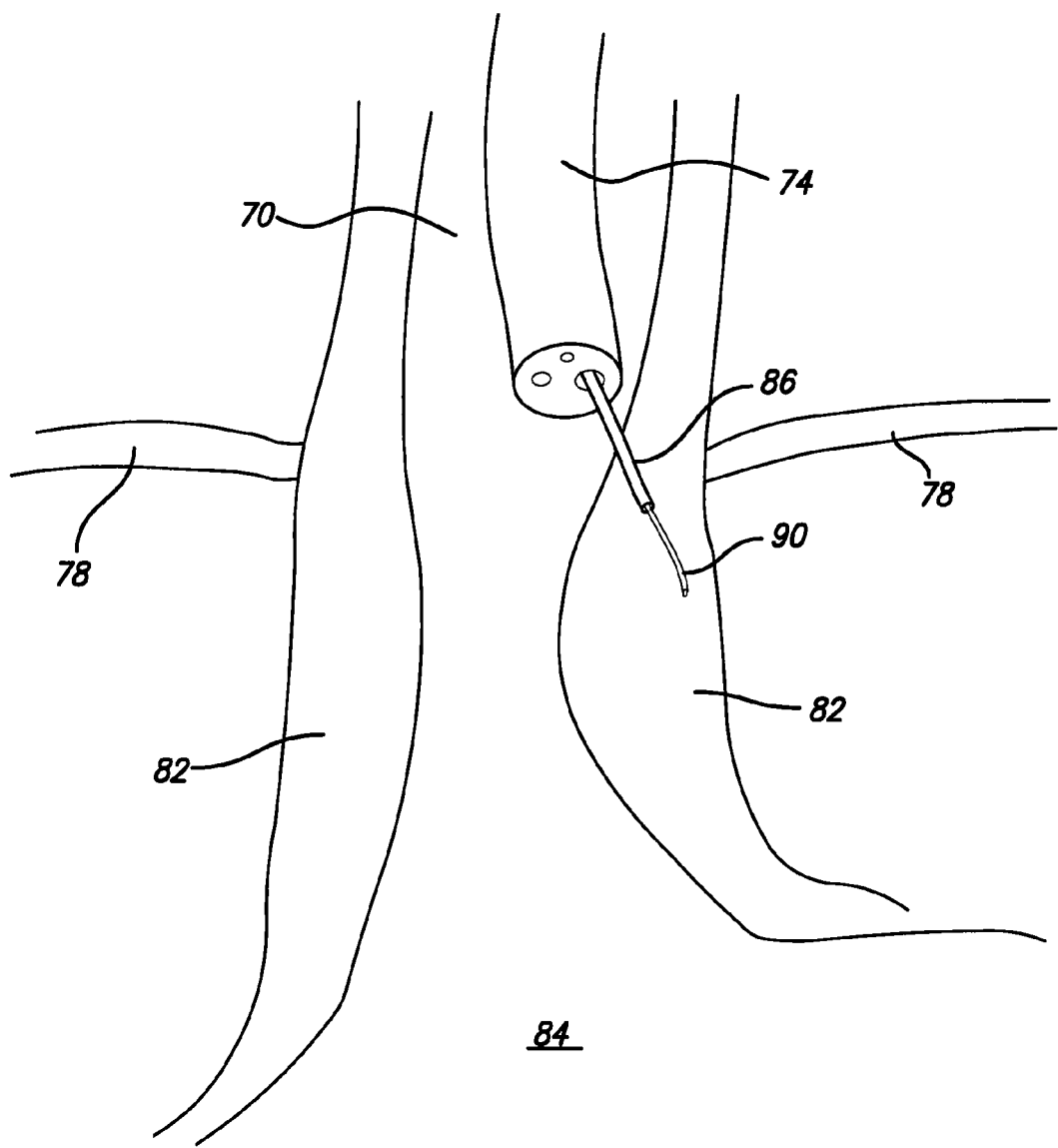
Figure 23:
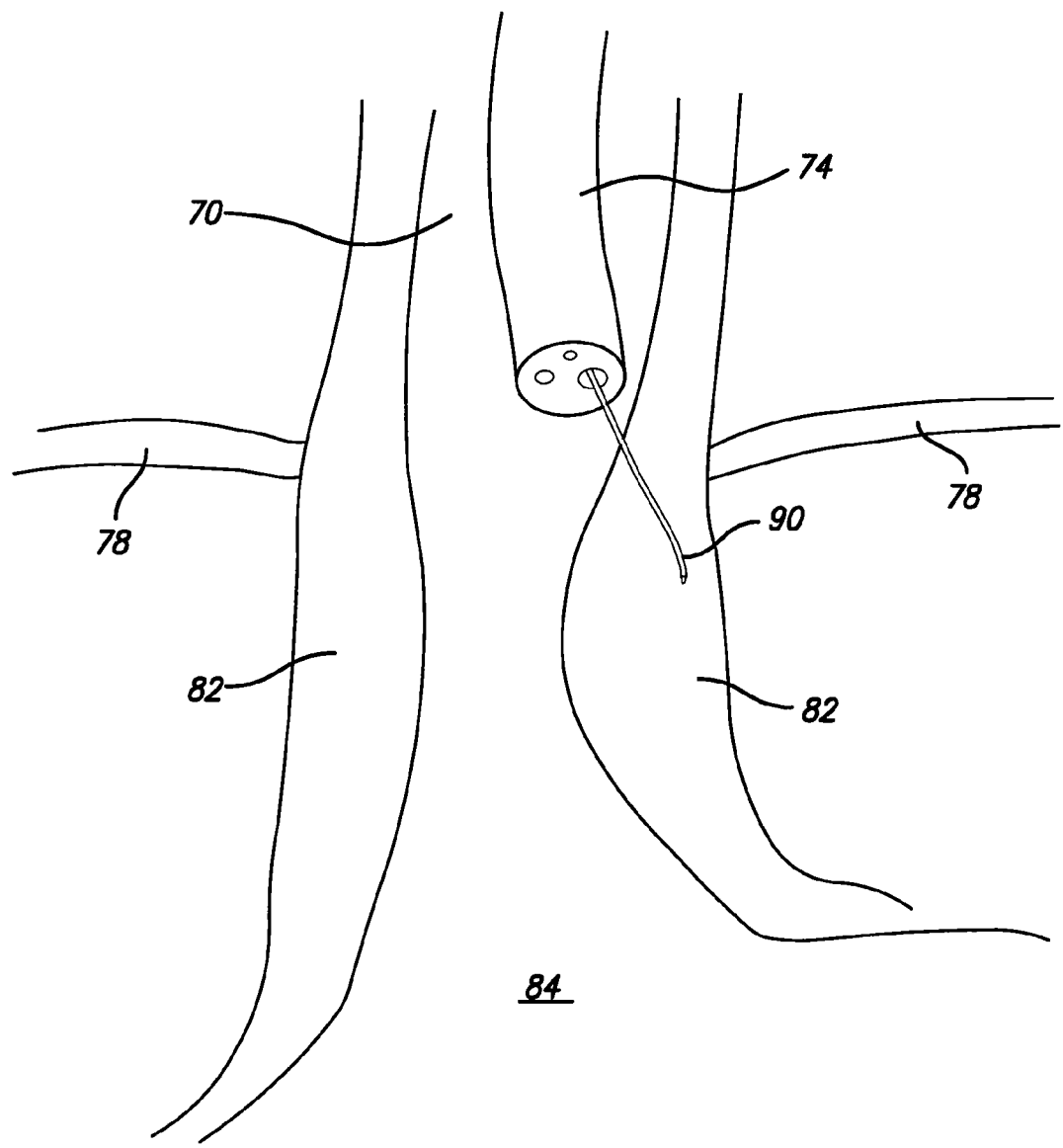
Figure 24:
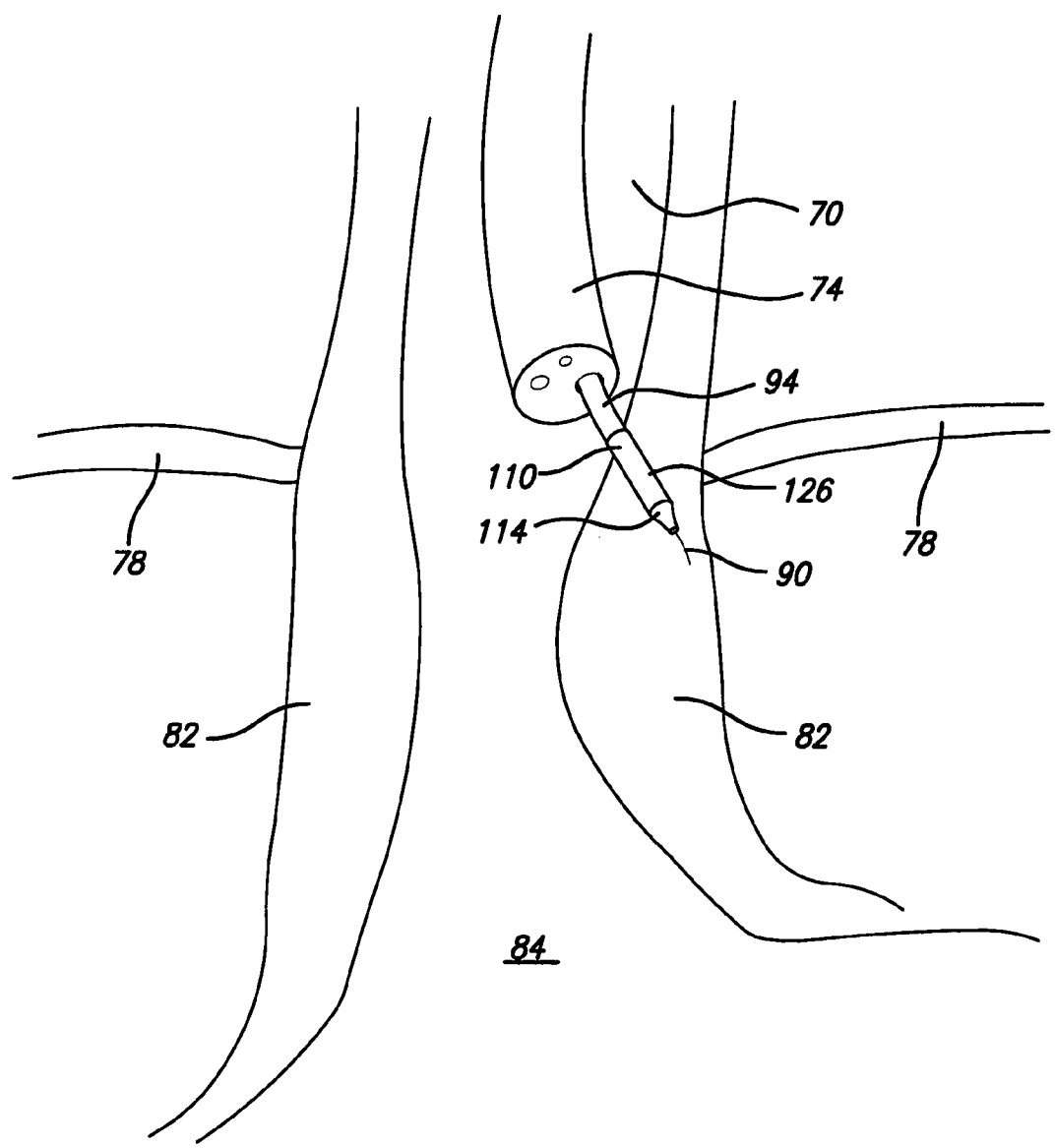
Figure 25:
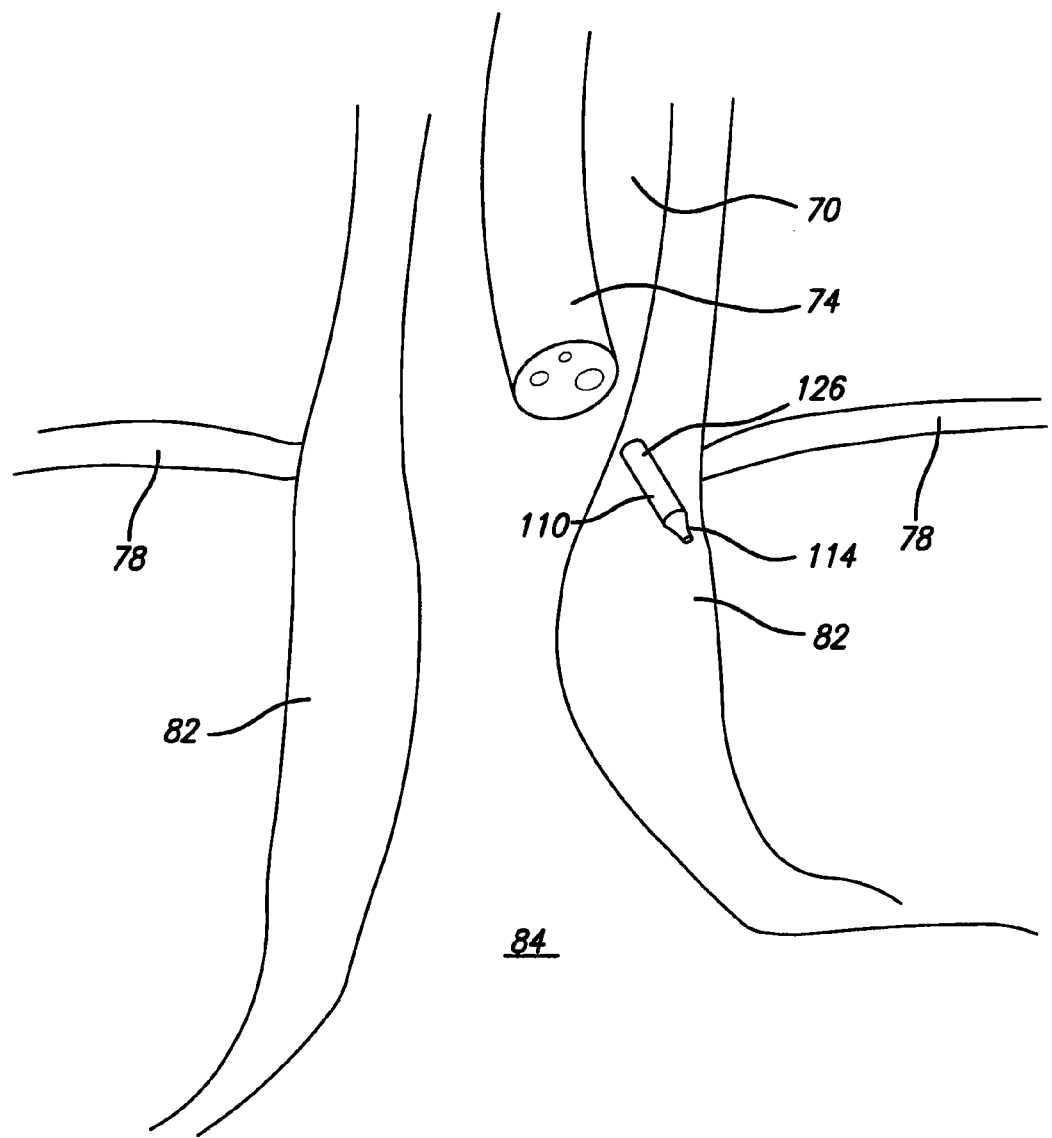
Figure 26:
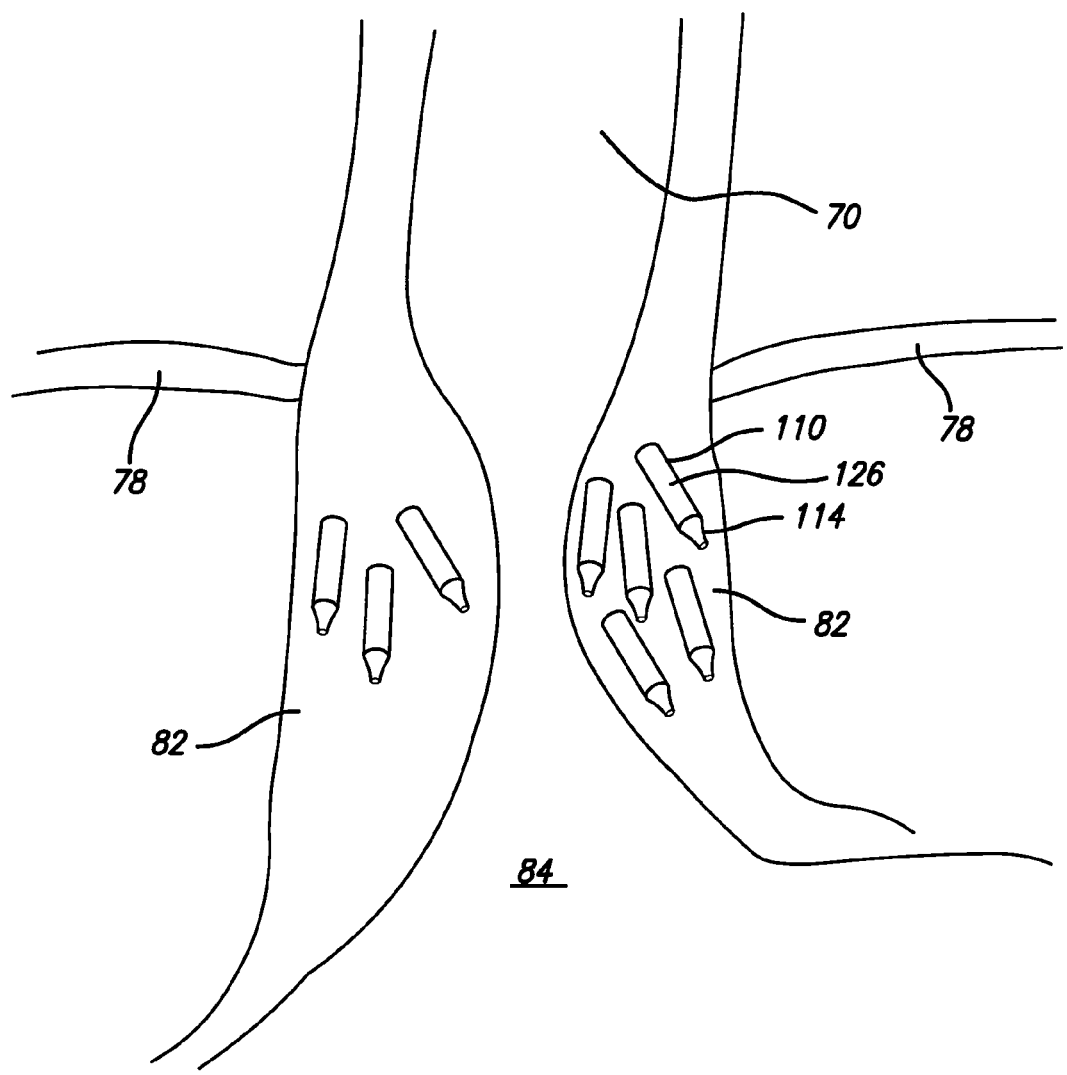

As shown in FIGS. 20-26, a preferred method of delivering the tipped implant generally includes first identifying the desired implant location with an endoscope and then inserting the tipped implant into that location. In particular, with reference to FIG. 20, endoscope 74 is passed through the mouth and esophagus 70 of a patient and delivered to the vicinity of LES 82. Thereafter, a needle 86 is passed through the working channel of endoscope 74, as shown in FIG. 21. Once needle 86 is located in a desired position within the LES 82, guidewire 90 is used to maintain access to the target tissue (FIG. 22). Guidewire 90 ultimately serves as a pilot for the delivery of the tipped implant into a precise location. Once the desired implant location is accessed by guidewire 90, needle 86 is removed (FIG. 23). The tipped implant 110 is subsequently threaded over guidewire 90 (FIG. 24). The tipped implant is then pushed along guidewire 90 toward the desired implant location. When the tipped implant reaches the target tissue, the tipped implant is pushed into the target tissue by conventional pusher tool 94. Once the tipped implant is in the target tissue, guidewire 90 is withdrawn (see FIG. 25). As illustrated in FIG. 26, this procedure may be repeated to insert as many tipped implants 110 as necessary for a given medical condition. Preferably, an ultrasound endoscope can be used to identify the target area and serve as a working channel for the delivery of the tipped implant. It should be noted that the tipped implant can alternatively be delivered without the use of a guidewire. For example, the tipped implant can be delivered into a target tissue through a cannula or catheter, or over a needle by using a conventional pusher instrument.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. Certainly, in view of the present disclosure, one skilled in the medical arts would be able to conceive of a wide variety of additional implant body shapes, tips, sizes, strings, and successful combinations thereof. Indeed, the selection of these and other details of construction are believed to be well within the ability of one of even rudimentary skills in this area, in view of the present disclosure. Likewise, one skilled in the medical arts would able to conceive of a wide variety of applications and uses for linked or tipped implants in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in *The American Heritage Dictionary*, third edition. All technical terms shall take on their customary meaning as established by the appropriate technical discipline utilized by those normally skilled in that particular art area. All medical terms shall take their meaning as defined by *Stedman's Medical Dictionary*, 27th edition.

What is claimed is:

1. A method of implanting a medical device into a target tissue for bulking the tissue, the method comprising:
    inserting a distal end of an elongate device comprising a needle into a target tissue, the needle having a lumen therethrough;
    providing a linked implant, the linked implant comprising a plurality of implant bodies and a first filament, the plurality of implant bodies disposed on the first filament;
    delivering the linked implant through the lumen into the tissue bulking the tissue by inserting the linked implant into the tissue; and
    withdrawing the elongate device.

2. The method of claim 1, further comprising delivering the elongate device to the target tissue through an endoscope.

3. The method of claim 1, further comprising inserting a guidewire into the target tissue to maintain access to the target tissue and withdrawing the needle.

4. The method of claim 3, further comprising delivering the elongate device over the guidewire and into the target tissue.

5. The method of claim 1, comprising providing one or more of the implant bodies comprising a passageway and inserting a guidewire through the passageway.

6. The method of claim 1, comprising providing a pusher tool inserted through the lumen of the elongate device to push the linked implant into the target tissue.

7. The method of claim 1, further comprising repositioning the elongate device and distributing the implant bodies throughout the target tissue.

8. The method of claim 1, comprising delivering the linked implant to the lower esophageal sphincter.

9. The method of claim 1, comprising providing the implant bodies on a net of filaments.

10. The method of claim 1, comprising providing the implant bodies on the filament so that the spacing between the implant bodies is non-uniform.

11. The method of claim 1, comprising providing the implant bodies comprising a bio-remodelable material.

12. The method of claim 11, comprising providing the implant bodies comprising an extracellular matrix.

13. The method of claim 11, comprising providing the implant bodies comprising submucosa.

14. The method of claim 1 comprising providing the implant bodies comprising one or more strips of material that are coiled together.

15. A method of implanting a medical device into a target tissue for bulking the tissue, the method comprising:
    providing a linked implant, the linked implant comprising a plurality of implant bodies and a first filament, the plurality of implant bodies disposed on the first filament, one or more of the implant bodies comprising a passageway therethrough;
    inserting a guidewire through the passageway;
    inserting a distal end of the guidewire into a target tissue;
    delivering the linked implant over the guidewire into the target tissue bulking the tissue by inserting the linked implant into the tissue; and
    withdrawing the guidewire.

16. The method of claim 15, comprising providing a pusher tool inserted through the lumen of the elongate device to push the linked implant into the target tissue.

* * * * *